(12) United States Patent
Cottone

(10) Patent No.: US 11,839,722 B2
(45) Date of Patent: Dec. 12, 2023

(54) PROGRESSIVE FLEXIBILITY CATHETER SUPPORT FRAME

(71) Applicant: OrbusNeich Medical PTE. LTD., Singapore (SG)

(72) Inventor: Robert J. Cottone, Davie, FL (US)

(73) Assignee: OrbusNeich Medical PTE. LTD., Singapore (SG)

( * ) Notice: Subject to any disclaimer, the term of this patent is extended or adjusted under 35 U.S.C. 154(b) by 1013 days.

(21) Appl. No.: 16/712,428

(22) Filed: Dec. 12, 2019

(65) Prior Publication Data

US 2020/0188633 A1 Jun. 18, 2020

Related U.S. Application Data

(63) Continuation of application No. 15/522,216, filed as application No. PCT/US2015/058969 on Nov. 4, 2015, now abandoned.

(60) Provisional application No. 62/238,428, filed on Oct. 7, 2015, provisional application No. 62/075,177, filed on Nov. 4, 2014.

(51) Int. Cl.
*A61M 25/00* (2006.01)
*A61M 25/01* (2006.01)
*A61M 25/06* (2006.01)

(52) U.S. Cl.
CPC .... *A61M 25/0069* (2013.01); *A61M 25/0023* (2013.01); *A61M 25/0043* (2013.01); *A61M 25/0045* (2013.01); *A61M 25/0051* (2013.01); *A61M 25/0054* (2013.01); *A61M 25/0102* (2013.01); *A61M 25/0662* (2013.01); *A61M 25/0013* (2013.01); *A61M 2025/006* (2013.01);
(Continued)

(58) Field of Classification Search
CPC .................. A61M 25/0054; A61M 25/0662
See application file for complete search history.

(56) References Cited

U.S. PATENT DOCUMENTS

| 4,552,554 A | 11/1985 | Gould et al. |
| 5,047,045 A | 9/1991 | Arney et al. |

(Continued)

FOREIGN PATENT DOCUMENTS

| CN | 101259014 A | 9/2008 |
| CN | 201279337 Y | 7/2009 |

(Continued)

OTHER PUBLICATIONS

Extended European Search Report of corresponding EP 19 860 216.1, dated Jan. 27, 2022.

(Continued)

*Primary Examiner* — Courtney B Fredrickson
(74) *Attorney, Agent, or Firm* — Leason Ellis LLP

(57) ABSTRACT

Cut-pattern designs creating a frame structure from a solid tube, which may be used as a portion of medical device, such as a catheter. The tube includes a plurality of units of cutout segments which are distributed in band around a circumference of the tube. A tube can have multiple different zones, each having units with varying cutout segments. The cutout segments can have varying cutout surface area allowing the flexibility of the tube to be modified at any point along the tube by altering the cutout surface area with zones having greater cutout surface areas as compared to another zone are more flexible. The tube can be incorporated into a catheter.

6 Claims, 33 Drawing Sheets

(52) U.S. Cl.
CPC .............. *A61M 2025/0047* (2013.01); *A61M 2205/0266* (2013.01)

(56) References Cited

U.S. PATENT DOCUMENTS

| | | |
|---|---|---|
| 5,102,403 A | 4/1992 | Alt |
| 5,120,323 A | 6/1992 | Shockey et al. |
| 5,152,744 A | 10/1992 | Krause et al. |
| 5,156,594 A | 10/1992 | Keith |
| 5,267,958 A | 12/1993 | Buchbinder et al. |
| 5,290,247 A * | 3/1994 | Crittenden .......... A61M 25/104 604/171 |
| 5,328,472 A | 7/1994 | Steinke et al. |
| 5,358,493 A | 10/1994 | Schweich, Jr. et al. |
| 5,385,562 A * | 1/1995 | Adams .............. A61M 25/0662 604/509 |
| 5,439,445 A | 8/1995 | Kontos |
| 5,507,751 A | 4/1996 | Goode et al. |
| 5,527,292 A | 6/1996 | Adams et al. |
| 5,545,151 A | 8/1996 | O'Connor et al. |
| 5,690,613 A | 11/1997 | Verbeek |
| 5,730,734 A | 3/1998 | Adams et al. |
| 5,769,829 A | 6/1998 | Mous |
| 5,776,141 A | 7/1998 | Klein et al. |
| 5,843,051 A | 12/1998 | Adams et al. |
| 5,865,815 A | 2/1999 | Tihon |
| 5,879,305 A | 3/1999 | Yock et al. |
| 5,921,957 A * | 7/1999 | Killion .............. A61M 25/0069 606/192 |
| 6,143,002 A | 11/2000 | Metmeier |
| 6,217,566 B1 | 4/2001 | Ju et al. |
| 6,338,725 B1 | 1/2002 | Hermann et al. |
| 6,520,951 B1 | 2/2003 | Carillo et al. |
| 6,599,274 B1 | 7/2003 | Kucharczyk et al. |
| 6,635,022 B2 | 10/2003 | Berg et al. |
| 6,638,268 B2 | 10/2003 | Niazi |
| 6,997,908 B2 | 2/2006 | Carillo, Jr. et al. |
| 7,025,751 B2 | 4/2006 | Silva et al. |
| 7,232,452 B2 | 6/2007 | Adams et al. |
| 7,367,967 B2 | 5/2008 | Eidenschink |
| D611,601 S | 3/2010 | Tamai et al. |
| 7,691,138 B2 | 4/2010 | Stenzel et al. |
| 7,744,585 B2 | 6/2010 | Carrillo, Jr. et al. |
| 7,762,984 B2 | 7/2010 | Kumoyama et al. |
| 7,854,743 B2 | 12/2010 | Palasis et al. |
| 7,887,529 B2 | 2/2011 | Eder |
| 7,972,294 B2 | 7/2011 | Nash et al. |
| 7,981,091 B2 | 7/2011 | Root et al. |
| 8,048,032 B2 | 11/2011 | Root et al. |
| 8,142,413 B2 | 3/2012 | Root et al. |
| 8,206,370 B2 | 6/2012 | von Oepen et al. |
| 8,292,850 B2 | 10/2012 | Root et al. |
| 8,372,056 B2 | 2/2013 | Eder |
| 8,613,706 B2 | 12/2013 | Langston |
| RE45,380 E | 2/2015 | Root et al. |
| 8,996,095 B2 | 3/2015 | Anderson et al. |
| 9,144,662 B2 | 9/2015 | Di Caprio et al. |
| RE45,760 E | 10/2015 | Root et al. |
| RE45,776 E | 10/2015 | Root et al. |
| 9,155,863 B2 | 10/2015 | Isaacson et al. |
| 9,332,914 B2 | 5/2016 | Langston |
| 9,352,123 B2 | 5/2016 | Zhou et al. |
| RE46,116 E | 8/2016 | Root et al. |
| 9,486,611 B2 | 11/2016 | Petersen et al. |
| 9,593,506 B2 | 3/2017 | Lockwood et al. |
| 9,687,634 B2 | 6/2017 | Grovender et al. |
| 9,764,118 B2 | 9/2017 | Anderson et al. |
| 9,993,613 B2 | 6/2018 | Wang et al. |
| 10,124,147 B2 | 11/2018 | Anderson et al. |
| 10,183,147 B2 | 1/2019 | Yang et al. |
| 10,188,396 B2 | 1/2019 | Folk et al. |
| 2002/0165598 A1 | 11/2002 | Wahr et al. |
| 2003/0195546 A1 | 10/2003 | Solar et al. |
| 2004/0010280 A1 | 1/2004 | Adams et al. |
| 2004/0127927 A1 | 7/2004 | Adams |
| 2004/0236215 A1 | 11/2004 | Mihara et al. |
| 2005/0004523 A1 | 1/2005 | Osborne et al. |
| 2005/0245896 A1 | 11/2005 | Kucharczyk et al. |
| 2006/0025752 A1 | 2/2006 | Broaddus et al. |
| 2006/0155367 A1 | 7/2006 | Hines |
| 2007/0038292 A1 | 2/2007 | Danielpour |
| 2007/0260219 A1 | 11/2007 | Root et al. |
| 2008/0077085 A1 | 3/2008 | Eidenschink et al. |
| 2008/0172008 A1 | 7/2008 | Root et al. |
| 2009/0043283 A1 | 2/2009 | Turnlund et al. |
| 2009/0318881 A1 | 12/2009 | Shennib |
| 2010/0010475 A1 | 1/2010 | Teirstein |
| 2010/0274158 A1 | 10/2010 | Teirstein |
| 2010/0331776 A1 | 12/2010 | Salahieh |
| 2011/0245808 A1 * | 10/2011 | Voeller .............. A61M 25/0054 604/528 |
| 2013/0006167 A1 | 1/2013 | Alvarez et al. |
| 2013/0116701 A1 | 5/2013 | Wang et al. |
| 2013/0123912 A1 | 5/2013 | Tung et al. |
| 2013/0158653 A1 | 6/2013 | Gamarra et al. |
| 2013/0197432 A1 | 8/2013 | Von Oepen |
| 2013/0197483 A1 | 8/2013 | Anderson et al. |
| 2013/0239959 A1 | 9/2013 | Brain |
| 2013/0289697 A1 | 10/2013 | Baker et al. |
| 2013/0331782 A1 | 12/2013 | Grovender et al. |
| 2014/0012281 A1 | 1/2014 | Wang et al. |
| 2014/0012355 A1 | 1/2014 | Ollivier et al. |
| 2014/0018773 A1 | 1/2014 | Wang et al. |
| 2014/0025004 A1 | 1/2014 | Falk et al. |
| 2014/0025043 A1 | 1/2014 | Wang et al. |
| 2014/0039461 A1 | 2/2014 | Anderson et al. |
| 2014/0052097 A1 | 2/2014 | Petersen et al. |
| 2014/0058324 A1 | 2/2014 | Salahieh et al. |
| 2014/0081243 A1 | 3/2014 | Zhou |
| 2014/0107610 A1 | 4/2014 | Witte |
| 2014/0171913 A1 | 6/2014 | Watanabe |
| 2014/0180122 A1 | 6/2014 | Stigall et al. |
| 2014/0276618 A1 * | 9/2014 | Di Caprio ......... A61M 25/0102 604/528 |
| 2015/0051584 A1 | 2/2015 | Korkuch |
| 2015/0133864 A1 | 5/2015 | Zachar et al. |
| 2015/0190617 A1 | 7/2015 | Anderson et al. |
| 2015/0282821 A1 * | 10/2015 | Look ................ A61B 17/32037 606/127 |
| 2015/0297863 A1 | 10/2015 | Hannon et al. |
| 2015/0352329 A1 | 12/2015 | Watanabe |
| 2016/0051799 A1 | 2/2016 | Daniels et al. |
| 2016/0066933 A1 | 3/2016 | Root et al. |
| 2016/0074627 A1 | 3/2016 | Cottone |
| 2016/0101261 A1 | 4/2016 | Kugler |
| 2016/0101262 A1 | 4/2016 | Root et al. |
| 2016/0121080 A1 | 5/2016 | Cottone |
| 2016/0242799 A1 | 8/2016 | Bonneau et al. |
| 2016/0346502 A1 | 12/2016 | Fuller et al. |
| 2016/0346509 A1 | 12/2016 | Anderson et al. |
| 2016/0346515 A1 | 12/2016 | Buller et al. |
| 2016/0346946 A1 | 12/2016 | Kasen |
| 2017/0014598 A1 | 1/2017 | Stursa et al. |
| 2017/0080178 A1 | 3/2017 | O'Connell et al. |
| 2017/0106160 A1 | 4/2017 | Zachar |
| 2017/0143355 A1 | 5/2017 | Nicholson et al. |
| 2017/0156750 A1 | 6/2017 | Root et al. |
| 2017/0246423 A2 | 8/2017 | Cottone |
| 2017/0252043 A1 * | 9/2017 | Fuller .............. A61B 17/12031 |
| 2017/0354800 A1 | 12/2017 | O'Donovan |
| 2018/0092650 A1 | 4/2018 | Kugler |
| 2018/0093070 A1 | 4/2018 | Cottone |
| 2018/0104445 A1 | 4/2018 | Fuller et al. |
| 2018/0161547 A1 | 6/2018 | Brenizer et al. |

FOREIGN PATENT DOCUMENTS

| | | |
|---|---|---|
| CN | 102949775 A | 3/2013 |
| CN | 103252014 | 8/2013 |
| CN | 103566455 A | 2/2014 |
| CN | 103623494 A | 3/2014 |
| CN | 104039384 A | 9/2014 |
| CN | 104093381 A | 10/2014 |
| CN | 104812420 A | 7/2015 |

(56) References Cited

FOREIGN PATENT DOCUMENTS

| | | |
|---|---|---|
| CN | 107148290 A | 9/2017 |
| EP | 1 656 963 A1 | 5/2006 |
| EP | 2124816 | 9/2009 |
| JP | H10507095 A | 7/1998 |
| JP | 2003525711 A | 9/2003 |
| JP | 2004275435 | 10/2004 |
| JP | 2005515797 A | 6/2005 |
| JP | 2008142351 A | 6/2008 |
| JP | 2008264118 A | 11/2008 |
| JP | 2015-523186 A | 8/2015 |
| WO | 1996/038193 | 12/1996 |
| WO | 2004/012804 A2 | 2/2004 |
| WO | 2007/035471 A2 | 3/2007 |
| WO | 2008/064280 | 5/2008 |
| WO | 2008/097545 A2 | 8/2008 |
| WO | 2009/020962 A1 | 2/2009 |
| WO | 2010/027662 A1 | 3/2010 |
| WO | 2010/136274 A1 | 12/2010 |
| WO | 2011/086758 A1 | 7/2011 |
| WO | 2012/151396 A2 | 11/2012 |
| WO | 2013/067180 A1 | 5/2013 |
| WO | 2013/070758 A2 | 5/2013 |
| WO | 2014/014644 A1 | 1/2014 |
| WO | 2014/015308 A1 | 1/2014 |
| WO | 2014/022310 A1 | 2/2014 |
| WO | 2014/028898 A2 | 2/2014 |
| WO | 2014/043694 A1 | 3/2014 |
| WO | 2014/0077881 | 5/2014 |
| WO | 2014/133897 A1 | 9/2014 |
| WO | 2014/141197 | 9/2014 |
| WO | 2015/157330 A1 | 10/2015 |
| WO | 2015/189354 A1 | 12/2015 |
| WO | 2016/011127 A2 | 1/2016 |
| WO | 2016064753 | 4/2016 |
| WO | 2016/073563 A1 | 5/2016 |
| WO | 2016/141025 A1 | 9/2016 |
| WO | 2016/172706 A1 | 10/2016 |
| WO | 2018/067824 A1 | 4/2018 |
| WO | 2018/075700 A1 | 4/2018 |
| WO | 2018/160966 A1 | 9/2018 |

OTHER PUBLICATIONS

Extended European Search Report of corresponding EP 21 19 0628.4, dated Jan. 27, 2022.
Extended European Search Report of corresponding EP 21 190 631.8, dated Jan. 27, 2022.
Extended European Search Report of corresponding EP 21 19 0650.8, dated Jan. 28, 2022.
Extended European Search Report of corresponding EP 21190661. 5, dated Feb. 1, 2022.
*Boston Scientific Corporation and Boston Scientific Scimed, Inc.* v. *Vascular Solutions, Inc.*, IPR2014-00761, Petition (May 16, 2014).
European Search Report dated Aug. 23, 2018 corresponding to European Patent Application No. EP15858019.
Takahashi et al., "New Method to Increase a Backup Support of a 6 French Guiding Coronary Catheter", Catheterization and Cardiovascular Interventions 63:452-456 (2004).
García-Blas et al., Usefulness and Safety of a Guide Catheter Extension System for the Percutaneous Treatment of Complex Coronary Lesions by a Transradial Approach, Med Princ Pract 2015;24:171-177.
*Vascular Solutions, Inc.*, v. *Boston Scientific Corporation*, 0:13-cv-01172-JRT-SER, Document 6 (D. Minn.) (May 28, 2013).
*Boston Scientific Corporation and Boston Scientific Scimed, Inc.* v. *Vascular Solutions, Inc.*, IPR2014-00760, Petition (May 16, 2014).
Theodore R. Kucklick, "The Medical Device R&D Handbook," 2006; pp. 1-139.
*Boston Scientific Corporation and Boston Scientific Scimed, Inc.* v. *Vascular Solutions, Inc.*, IPR2014-00762, Petition (May 16, 2014).
*Boston Scientific Corporation and Boston Scientific Scimed, Inc.* v. *Vascular Solutions, Inc.*, IPR2014-00759, Petition (May 15, 2014).
*QXMédical, LLC,* v. *Vascular Solutions, Inc.*, 0:17-cv-01969-PJS-TNL, Complaint (Jun. 8, 2017).
*Boston Scientific Corporation and Boston Scientific Scimed, Inc.* v. *Vascular Solutions, Inc.*, IPR2014-00763, Corrected Petition (May 16, 2014).
U.S. Appl. No. 14/984,273, filed Dec. 30, 2015, which is a reissue of U.S. Pat. No. 8,292,850.
International Search Report and Written Opinion dated Feb. 4, 2016 corresponding to International Patent Application No. PCT/US2015/058969.
Japanese Office Action dated Jun. 11, 2019 corresponding to Japanese patent application JP 2017-519694, with English translation.
Chinese Office Action and Search Report dated Aug. 2, 2019 corresponding to Chinese patent application CN 201580059920.3, with English translation.
Extended European Search Report and Written Opinion dated May 8, 2020 corresponding to European patent application EP 19 196 012.9.

\* cited by examiner

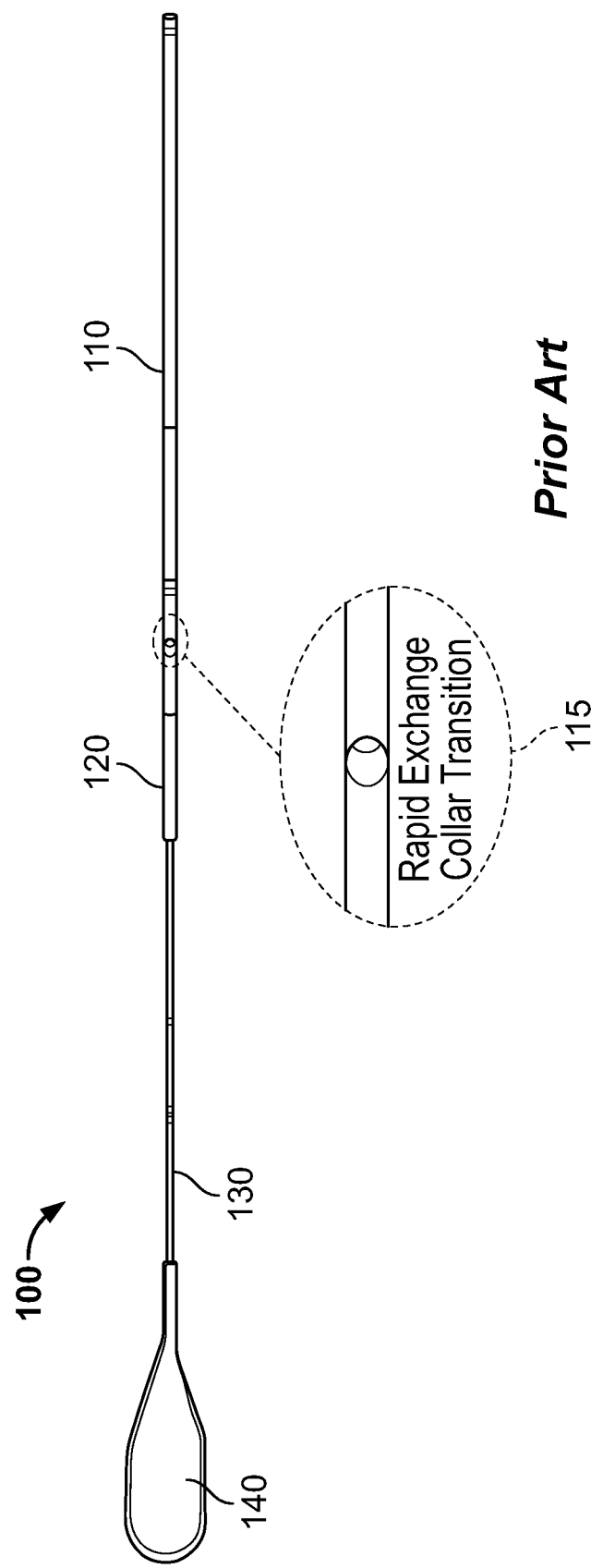

Zone 4

Zone 3

Zone 2

Zone 1

Zone 7

Zone 6

Zone 5

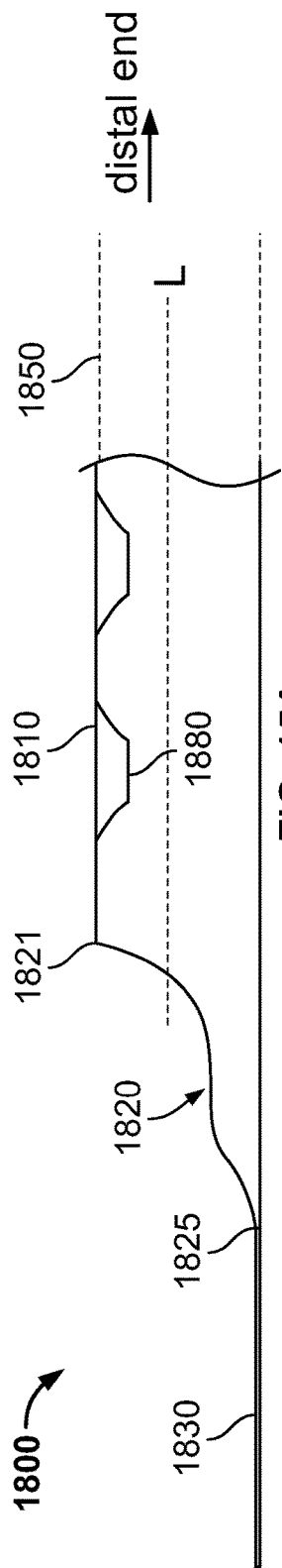
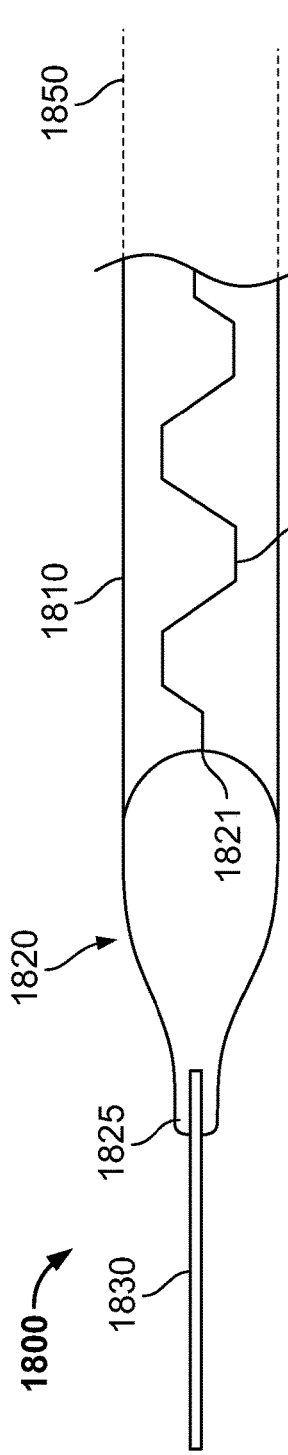
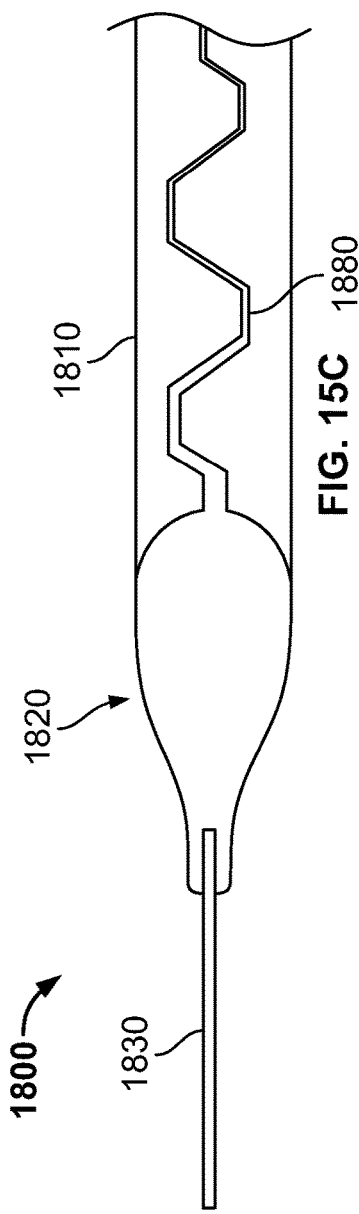
FIG. 15A
FIG. 15B
FIG. 15C

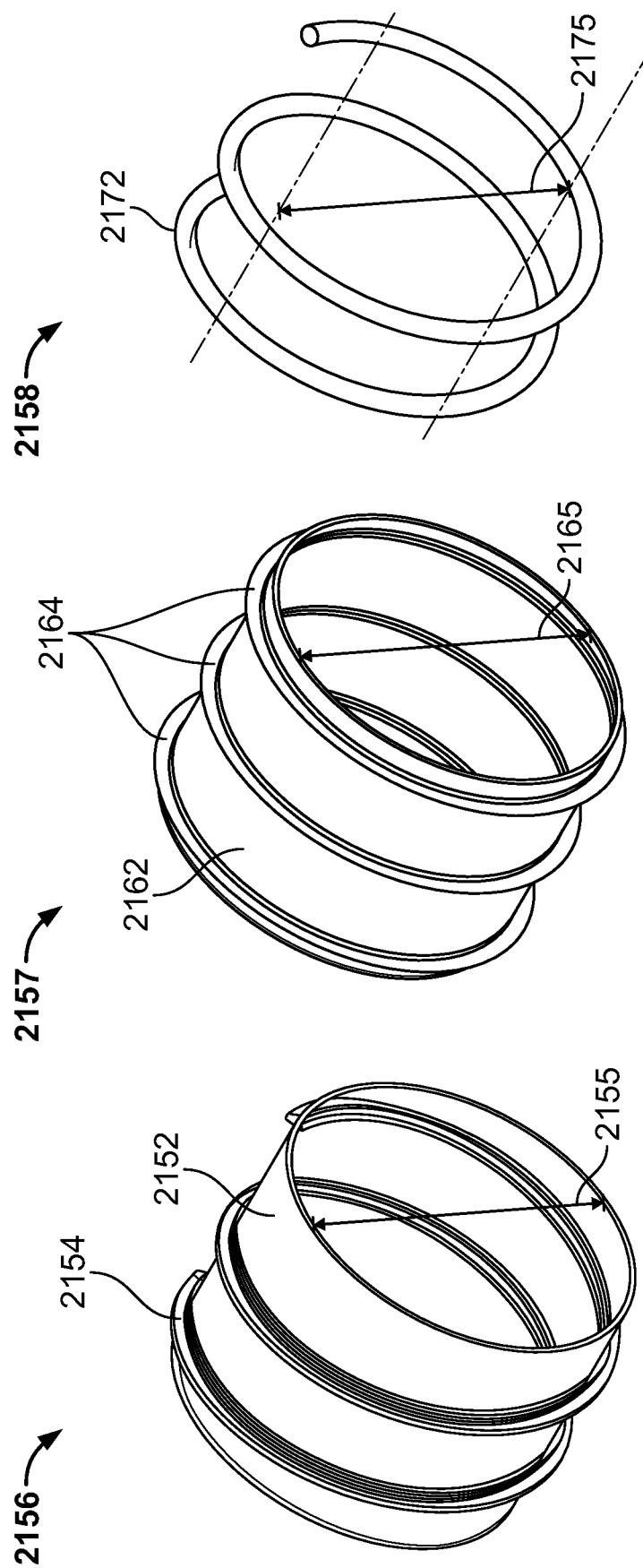

PROGRESSIVE FLEXIBILITY CATHETER SUPPORT FRAME

CROSS REFERENCE TO RELATED APPLICATION

This application claims priority to U.S. Provisional Application No. 62/075,177, filed Nov. 4, 2014, and U.S. Provisional Application No. 62/238,428, filed Oct. 7, 2015, the disclosures of which are incorporated by reference herein in their entirety.

FIELD OF THE INVENTION

The invention relates to a series of cut-pattern designs which create a frame structure from a solid tube and which may be used as a portion of medical device, such as a catheter.

BACKGROUND

In coronary artery disease, the coronary arteries may be narrowed or occluded by atherosclerotic plaques or other lesions. These lesions may totally obstruct the lumen of the artery or may dramatically narrow the lumen of the artery. In order to diagnose and treat obstructive coronary artery disease it is commonly necessary to pass a guidewire or other instruments through and beyond the occlusion or stenosis of the coronary artery.

Percutaneous coronary intervention (PCI), also known as coronary angioplasty, is a therapeutic procedure used to treat the narrowed or stenotic section of the coronary artery of the heart due to coronary lesions or obstructions. A guide catheter may be used in PCI to provide support an easier passage for another catheter or device (microcatheter, stents, balloons, etc.) to access the target site. For example, a guide catheter can be inserted through the aorta and into the ostium of the coronary artery. Once seated in the opening or ostium of the artery to be treated, a guidewire or other instrument is passed through the lumen of the guide catheter and then inserted into the artery distal to the occlusion or stenosis. Another example for the use of a guide catheter is shown where the guide catheter can be inserted through the aorta and into the peripheral anatomy enabling access, for example, to the femoral artery down through the popliteal artery. This procedure allows for access to vasculature below the knee.

However, guide catheters may encounter certain difficulties. The anatomy in the area for placement, e.g., the coronary vasculature, may be tortuous and the lesions themselves may be comparatively non-compliant. Moreover, when crossing comparatively non-compliant lesions, a backward force sufficient to dislodge the guide catheter from the ostium of the artery being treated can be generated. For example, in order to improve backup support, U.S. Re. 45,830, assigned to Vascular Solutions, Inc., discloses a coaxial guide catheter which is adapted to be passable within a guide catheter. The distal portion of the coaxial guide can be extended distally from the distal end of the guide catheter. The coaxial guide catheter includes a flexible tip portion defining a tubular structure having a lumen through which interventional cardiology devices such as stents and balloons can be inserted and a substantially rigid portion proximal of and more rigid than the flexible tip portion that defines a rail structure without a lumen.

Facilitating equipment delivery is the most common indication for using a guide catheter. Other indicates include, thrombectomy, facilitating interventions in chronic total occlusion (CTO)s and selective contrast injection into the vasculature. Duaong et al. *J. Invasive Cardiol* 27(10):E211-E215 (2015).

As illustrated in FIG. 1A, which is a depiction of a commercial product "Guideliner®" from Vascular Solutions, Inc., a guide catheter extension 100 includes a distal portion 110 having a full circumference, a half-pipe portion 120, a collar transition 115 which provides a rapid-exchange type access point to insert interventional devices (e.g., balloons, stents, etc.), a push rod 130, and a proximal tab 140 for manual manipulation of the guide catheter extension 100.

Another device is Guidezilla® from Boston Scientific Corp. FIG. 1B depicts a commercial guide catheter extension product. Compared to FIG. 1A, this product lacks an explicit half-pipe section, and instead uses a skived or tapered collar transition which is directly connected to a push rod or rail.

To date the guide catheter extension devices disclosed or available requires construction of different tube portions of different characteristics and joining these tube portions together. For example, as disclosed in U.S. Re 45,830, the catheter extension includes a soft tip, a reinforced portion that is made of braided or coil reinforced polymeric section (e.g., PTFE (polytetrafluoroethylene) (liner and Pebax as the exterior), and a substantially rigid portion which may be made of stainless steel or nitinol tube. For the Guidezella® catheter, the collar transition is made of a different material than the tubular portion which has a reinforced portion formed from multi-filament braided wire to reinforced the polymeric section. This structure makes fabrication complicated.

Prior art designs for catheter tube bodies that have varying degrees of flexibility along the long or longitudinal axis often employ spiral cuts or interrupted spiral cuts along part of the tube segment. Parameters of the spiral cuts, such as cut pitch angle, cut widths, cut lengths, etc., are varied in order to provide the varying degrees of flexibility to the catheter shaft.

However, there remains a need for improved design for catheter extensions, and more generally, alternative designs for catheter tubes, that allow not only ease of fabrication, but also control of various characteristics of the tube, e.g., steerability, variable bending flexibility along the working length, pushability, collapse or kink resistance, etc., at any point along the tube.

SUMMARY OF THE INVENTION

The invention provides for a tube, comprising, at least one zone positioned along a portion of the length of the tube, the zone comprising a plurality of units, where the units of the zone are distributed circumferentially around the tube in at least one first band, each unit of the zone comprises at least one cutout segment that is oriented around a center of symmetry, where the center of symmetry of each unit in the band is positioned equally from the center of symmetry of an adjacent unit in the same band and the center of symmetry of each unit is positioned at the same point on the circumference of the tube as the center of symmetry of a second unit in a third band which is separated by one band from the first band. The tube could have 2-100 zones and there can be 2-1000 bands in each zone.

In one embodiment, the unit comprises three cutout segments extending radially from a center of symmetry of the unit, where each cutout segment of the unit is positioned 120° degrees from the other cutout segments in the unit in the band. In this three cutout embodiment, there can be seven zones, a first zone, a second zone, a third zone, a fourth zone, a fifth zone, a sixth zone and a seventh zone, each zone is formed from a plurality of units, where rank order of cutout surface area and cut-pattern perimeter length is: units of the first zone<unit of the second zone<unit of the third zone<unit of the fourth zone<unit of the fifth zone<unit of the sixth zone<unit of the seventh zone. The zones can be arranged in sequence as first zone, second zone, third zone, fourth zone, fifth zone, sixth zone and seventh zone.

Alternatively, the cutout segments are in the shape of a hexagon. This hexagon cutout embodiment can have seven zones, a first zone, a second zone, a third zone, a fourth zone, a fifth zone, a sixth zone and a seventh zone, each zone is formed from a plurality of units, where rank order of cutout surface area and cut-pattern perimeter length is: unit of the first zone<unit of the second zone<unit of the third zone<unit of the fourth zone<unit of the fifth zone<unit of the sixth zone<unit of the seventh zone.

The tube can be made from a metallic material, such as nitinol or stainless steel.

The tube can further comprise a section which has a spiral cut section along a portion of the length of the tube and the spiral cut section can be contiguous with the zone of the tube. The spiral cut section may be an interrupted spiral cut.

In another embodiment, the cutout segments are in the shape of a circle.

The invention comprises a guide catheter extension comprising: a tube comprising, at least one zone along a portion of the length of the tube, the zone comprising a plurality of units, where the units of the zone are distributed circumferentially around the tube in at least one band, each unit of the zone comprises at least one cutout segment that is oriented around a center of symmetry, where the center of symmetry of each unit in the band is positioned equally from the center of symmetry of an adjacent unit in the same band; a skived collar transition section disposed adjacent the tube, the transition section having a tapered edge, a short end and a long end; and a push rod attached at the long end of the transition section. In this embodiment, each unit comprises three cutout segments extending radially from a center of symmetry of the unit, where each cutout segment of the unit is positioned 120° degrees from the other cutout segments in the unit in the band. The tube can comprise seven zones, a first zone, a second zone, a third zone, a fourth zone, a fifth zone, a sixth zone and a seventh zone, each zone having is formed from a plurality of units, wherein rank order of cutout surface area and cut-pattern perimeter length is: unit of the first zone<unit of the second zone<unit of the third zone<unit of the fourth zone<unit of the fifth zone<unit of the sixth zone<unit of the seventh zone. The zones can be arranged in sequence as first zone, second zone, third zone, fourth zone, fifth zone, sixth zone and seventh zone.

In another embodiment, the cutout segments are in the shape of a hexagon in tube of the guide catheter extension.

In a further embodiment, the guide catheter extension can comprise: a tube comprising, at least one zone along a portion of the length of the tube, the zone comprising a plurality of units, where the units of the zone are distributed circumferentially around the tube in at least one band, each unit of the zone comprises at least one cutout segment that is oriented around a center of symmetry, where the center of symmetry of each unit in the band is positioned equally from the center of symmetry of an adjacent unit in the same band; a flared bib, that is substantially perpendicular to the long axis of the tube, which has a greater diameter than the outer diameter of the tube; and, a push rod attached at the long end of the transition section.

In various embodiments, the diameter of the tube can taper from a proximal end to a distal end.

The tube of the guide catheter extension can further comprise a section where the tube has a spiral cut section along a portion of the length of the tube and the spiral cut section is contiguous with the zone of the tube. The spiral cut section can be an interrupted spiral cut.

BRIEF DESCRIPTION OF THE DRAWINGS

FIG. 1A depicts a prior art catheter extension device.

FIG. 15A is a schematic side view of a guide catheter extension having a generally longitudinal cut according to certain embodiments of the present invention.

FIG. 15B is a schematic top view of the guide catheter extension shown in FIG. 15A.

FIG. 15C is a schematic top view of the guide catheter extension when split open along the longitudinal cut shown in FIGS. 15A and 15B.

FIG. 17B-17D show various configurations of a sealer according to certain embodiments of the present invention.

DETAILED DESCRIPTION

The present invention generally relates to multiple cut-pattern designs for a tubular structure (or tube) of a medical device for interventional procedures that can be passed through a portion of a patient's vasculature or into other body lumens, such as guiding catheters, guide catheter extensions, micro-catheters, as well as other catheter tubes. A tube (or a portion thereof) may be substantially uniform in diameter across its entire length. Alternatively, the tube can have a varying diameter across its length, e.g., a tapered configuration. The tapering can be in any direction and may only be present along a portion of the tube. The tube can be made from a metallic material (e.g., stainless steel) or metal alloy, for example, a shape memory material such as nitinol which renders the tube kink resistant. Alternatively, the tube can be formed from polymers, glass filled polymers or a metal-polymer composite. The exterior surface of tube, which can have the desired cut or etched patterns, can be further encapsulated or covered with a polymeric jacket material, and the inner surface of the tube can be lined with a polymer inner lining which has a smooth, lubricous surface.

Figure 1B:
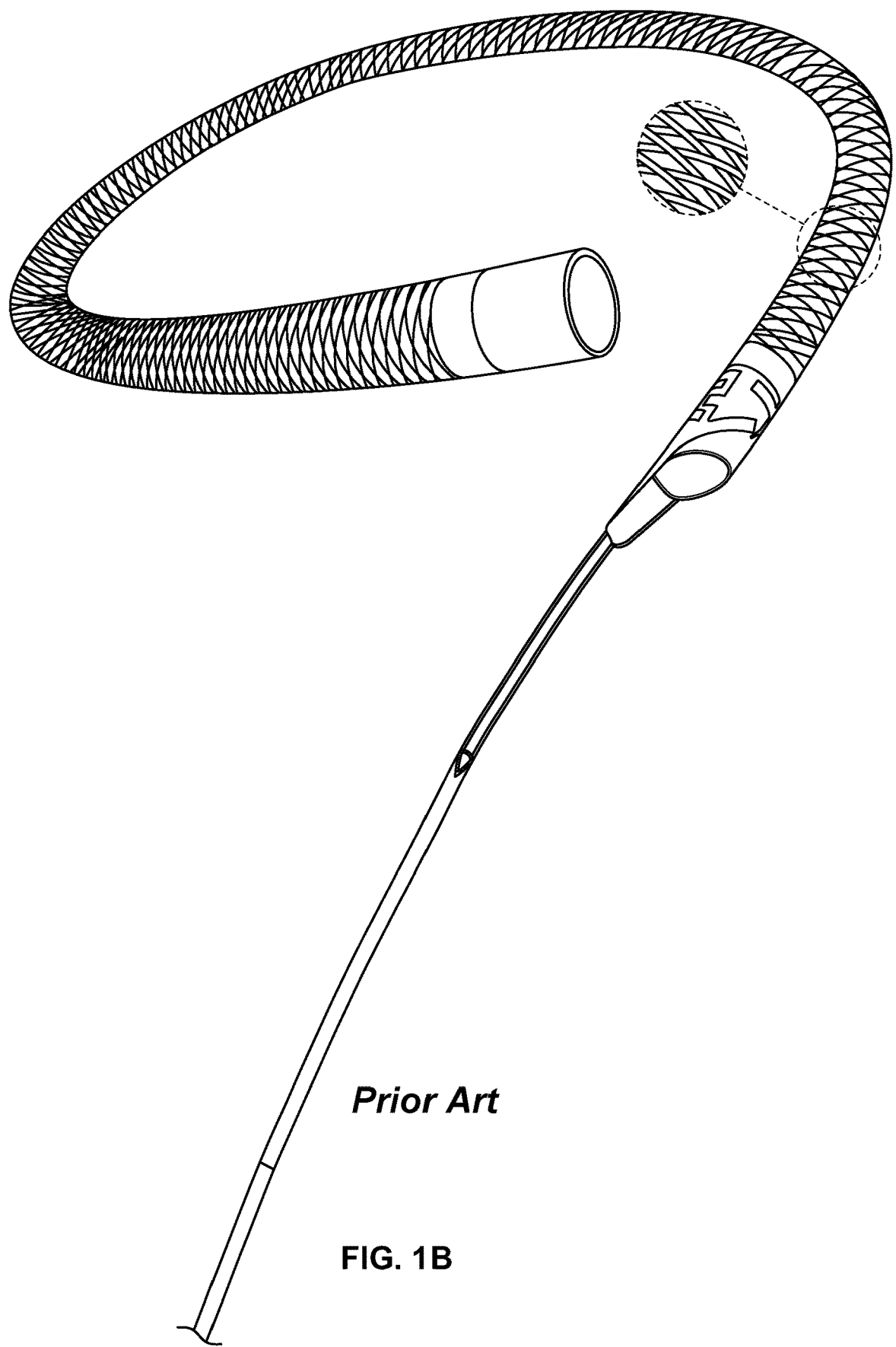
FIG. 1B depicts another prior art catheter extension device.
Figure 2A:
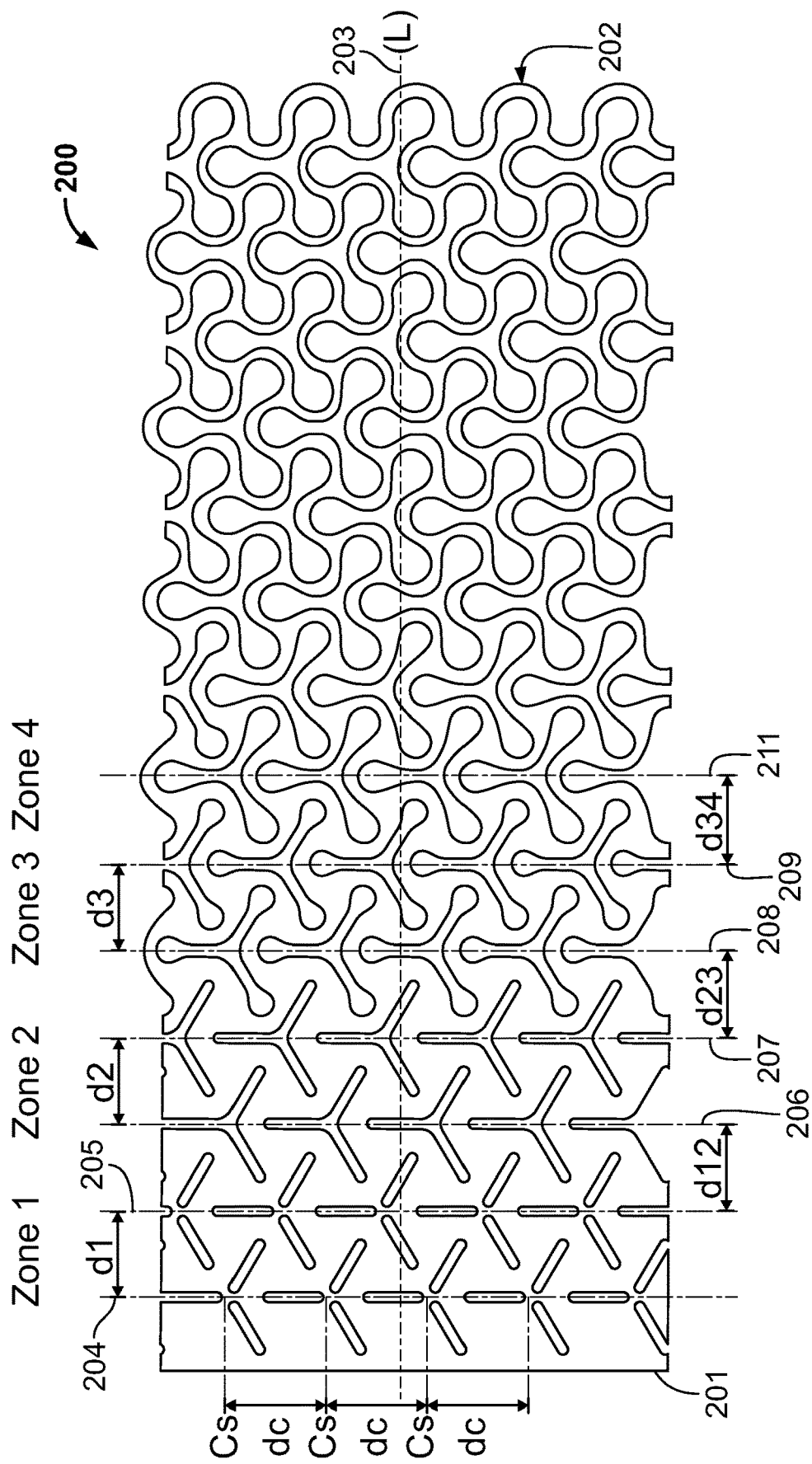
FIG. 2A is an unrolled or flat view of a tube having triplex cut patterns according to some embodiments of the present invention.
Figure 2B:
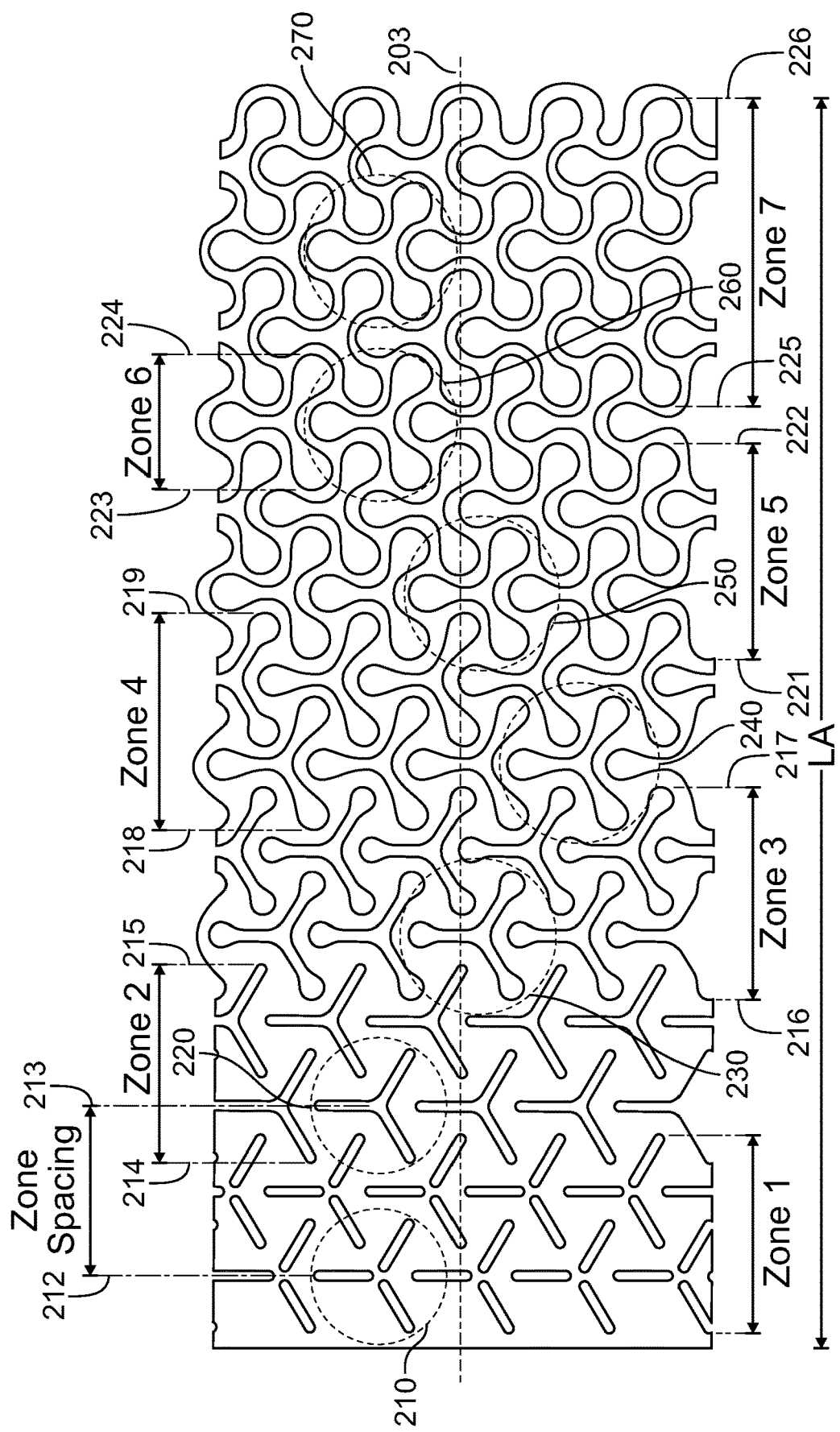
FIG. 2B is another unrolled or flat view of a tube having triplex cut patterns as depicted in FIG. 2A, which includes 7 triplex zones (Zone 1 to Zone 7).

One embodiment of the tube cut patterns of the invention is shown in FIGS. 2A and 2B. A tube 200 having a longitudinal axis 203 (L), a proximal end 201, a distal end 202, and a body or tube wall. The tube wall has cut patterns which include a plurality of zones, 1-7, which are arranged along the longitudinal axis L. The zones can be along any portion of the tube or a single zone may comprise the entire tube. The length of the tube is shown as LA. Each zone includes a plurality of units (or groups) of radially symmetric, cutout segments that are distributed around the circumference of the tube in a band or row. A band or row can have 2, 3, 4, 5, 6, 7, 8, 9, 10, 20, 30, 40, 50, 60, 70, 80, 90, 100, 200, 300, 400, 500, 1000 to n units. In FIGS. 2A and 2B there are 5 units in each band or row. The number of units per band or row may be the same or different in two different zones. As shown in FIG. 2B, a unit from each of the 7 zones is identified as 210, 220, 230, 240, 250, 260, 270, respectively. Each unit of the cutout portions can include three cutout segments each segment extending radially from a center point or center of symmetry. The cutout segments have a three-fold rotational symmetry, where each cutout segment is rotated 120 degrees from an adjacent cutout segment about a center of symmetry. Within each zone, all of the units of cutout segments may have an equal open surface area (i.e., the open surface area is the area enclosed by the contour of the segments in a contiguous manner) as well as an equal cut-pattern perimeter length, the length of a continuous line traced along the shape of the cutout segment. Across different zones, the units of cutout segments may have larger surface areas and increased cut-pattern perimeter length in zones when labeled in the figure with higher zone numbers, e.g., the open surface area ranking unit of zone 1<unit of zone 2<unit of zone 3<unit of zone 4<unit of zone 5<unit of zone 6<unit of zone 7 and the cut-pattern perimeter length ranking is unit of zone 1<unit of zone 2<unit of zone 3<unit of zone 4<unit of zone 5<unit of zone 6<unit of zone 7. The patterns of the cutout portions having the three-fold rotational symmetry about a central point of symmetry (center of symmetry) as shown can also generally referred to as the "triplex" pattern or "triplex" cut herein.

In FIG. 2A-2B, the triplex zones 1-7 are shown as being arranged sequentially along the longitudinal axis 203 of the tube having a length LA. The configuration shown provides for a gradually decreasing uncut surface area coverage along the length of the tube from the proximal end 201 to the distal end 203, enabling the tube 200 to have a gradually increasing bending flexibility from the proximal end 201 to the distal end 203. The 7 zones in FIG. 2B are shown arranged in sequence, i.e., 1 to 7, only for illustrative purpose. In other embodiments, the zones containing the units can be arranged in any order along the longitudinal axis to provide any desired change of bending flexibility at any point or section along the longitudinal axis. The tube can be provided with fewer, 1, 2, 3, 4, 5 or 6, or more zones, 7, 8, 9, 10, 11, 12, 13, 14 or 15 (higher numbers are also possible, e.g. 20, 30, 40, 50, 60, 70, 80, 90, 100, 200, 300, 400, 500, 600, 700, 800, 900, 1000 to n different zones). The zones, which have different cutout surface areas as well as different cut-pattern perimeter lengths, can also be arranged in any order, e.g., zone 1, zone 6, zone 7, zone 4, zone 5, zone 3, zone 2, in order to control flexibility of the tube at any point along the length of the tube.

As shown in FIGS. 2A-2B, each of zones 1-5 can include two adjacent rows or bands (as used herein, the term, row or rows is used interchangeably with the term band or bands) of units of cutout segments (e.g., bands in zone 1 and bands in zone 2 are shown as 204, 205 and 206, 207, respectively, FIG. 2A) each arranged around the circumference of the tube. The rows or bands may also be referred to as circumferential rows or bands. In a row or band, the units are distributed in a straight line around the circumference of the tube. For illustration only, the band comprising the units of zone 1 and zone 2 are shown with a dotted line through the center of each band intersecting the center of symmetry (Cs) for each unit; for zone 1, the dotted lines are 204 and 205, while for zone 2, the dotted line is 206 (FIG. 2A). Other numbers of bands/rows of units in a zone are also possible, including, 1, 2, 3, 4, 5, 6, 7, 8, 9, 10, 20, 30, 40, 50, 60, 70, 80, 90, 100, 200, 300, 400, 500, 1000 up to n bands or rows.

The spacing between units in a band is shown in FIG. 2A and is represented as dc, where dc is the distance between the center of symmetry, Cs, of two adjacent units in the same band (see, e.g., 204). The spacing, dc, is equal within a single band and may be constant across the length of the tube in different zones. The spacing between bands within a zone, e.g., zone 1, zone 2 and zone 3, is shown as d1 (204-205), d2 (206-207) and d3 (208-209); d1=d2=d3, where the spacing is measured between the lines, 204, 205, 206, 207, 208 and 209, which run through the center of symmetry, Cs, of the bands within each zone. The spacing between zones, e.g., zone 1-zone 2, d12 (205-206), zone 2-zone 3, d23 (207-208) and zone 3-zone 4, d34 (209-211); d12=d23=d34, where the spacing is measured between the lines, 204, 205, 206, 207, 208, 209 and 211. In one embodiment, the spacing between bands within a zone may be equal to the spacing of two bands between two different zones, e.g., d1=d2=d3=d12=d23=d34. In other embodiments, the spacing between bands within a zone may be greater than or less than the spacing between the bands in two different zones, e.g., d1=d2=d3>d12=d23=d34 or d1=d2=d3<d12=d23=d34.

The overall arrangement of one embodiment of the tube is shown in FIG. 2B. The boundaries of each zone are shown as follows: zone 1, 212, 213, zone 2, 214, 215, zone 3, 216, 217, zone 4, 218, 219, zone 5, 221, 222, zone 6, 223, 224 and zone 7, 225, 226. The boundaries of the zones overlap with each other. The units within each zone are shown as zone 1, 210, zone 2, 220, zone 3, 230, zone 4, 240, zone 5, 250, zone 6, 260 and zone 7, 270.

Figure 2C:
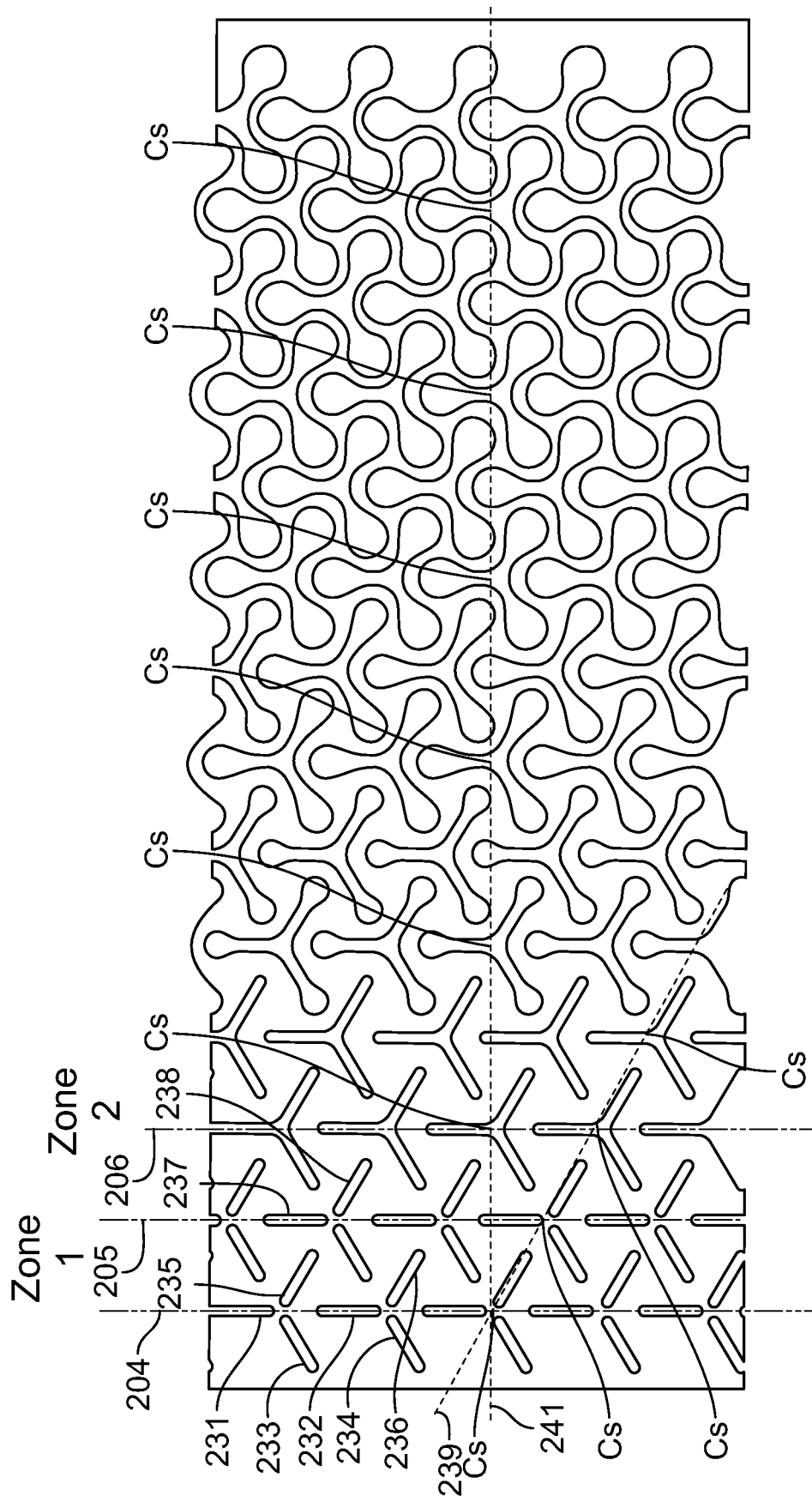
FIG. 2C is another unrolled or flat view of a tube in FIG. 2A.
Figure 2D:
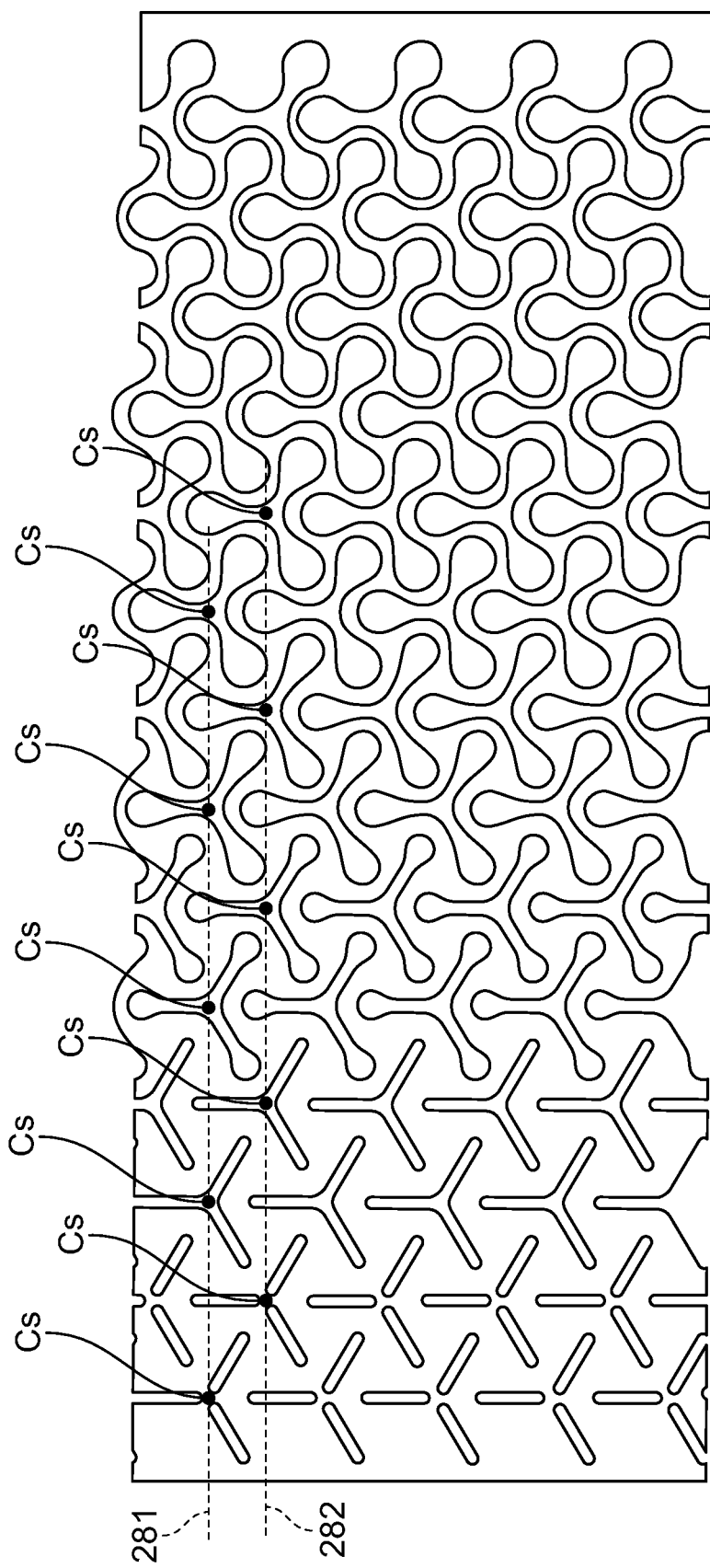
FIG. 2D is another unrolled or flat view of a tube in FIG. 2C showing the center of symmetry across the tube.

As shown in FIG. 2A-2C, all cutout segments of the units within a zone can have the same orientation or are in-phase with respect to the line through the center of symmetry for each row, 204 and 205; compare cutout segments 231-232, 233-234 and 235-236. The cutout segments in adjacent bands or rows within a zone can also have the same orientation or are in-phase with respect to the line through the center of symmetry for each row, 204 and 205; compare, 231-237 and 235-238. In other words, the corresponding cutout segments in one unit within a zone are parallel with the cutout segments in an adjacent unit. The center of symmetry, Cs, of units within the same zone, but in adjacent bands is shifted by one unit as shown in FIG. 2C. Between two adjacent zones, e.g., zone 1 and zone 2, the units are shifted around the circumference of the band such that a straight line, 239, can be drawn between the center of symmetry for units in the same zone or adjacent zones in every other band, e.g., 1, 3, 5, 7, etc. bands. The center of symmetry, Cs, in different bands falls along the same line in every other band. FIG. 2D—reference lines 281 and 282. In other words, the center of symmetry of each unit is positioned at the same point on the circumference of the tube as the center of symmetry of a second unit in a third, third, fifth, etc. band which is separated by one band from the first band.

Depending on the material as well as the structural requirements in terms of flexibility, the thickness of the tube at any point can vary, e.g., from about 0.05 mm to 2 mm, e.g., 0.05 mm to about 1 mm, about 0.1 mm, 0.2 mm, 0.3 mm, 0.4 mm, 0.5 mm, 0.6 mm, 0.7 mm, 0.8 mm, 0.9 mm, 1.0 mm, etc. The inner diameter of the lumen (ID) of the tube portion can vary, e.g., from about 0.1 mm to about 2 mm, or from about 0.25 mm to about 1 mm, e.g., about 0.2 mm, about 0.3 mm, about 0.4 mm, about 0.5 mm, about 0.6 mm, about 0.7 mm, about 0.8 mm, about 0.9 mm, about 1 mm, etc. The outer diameter of the lumen (OD) of the tube can also vary, e.g., from about 0.2 mm to about 3 mm, e.g., about 0.2 mm, about 0.3 mm, about 0.4 mm, about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2.0 mm, etc. The thickness of the tube wall, the inner diameter ID and the outer diameter OD can each be constant throughout the length of the tube, or vary along the length of the tube.

Figure 3A:
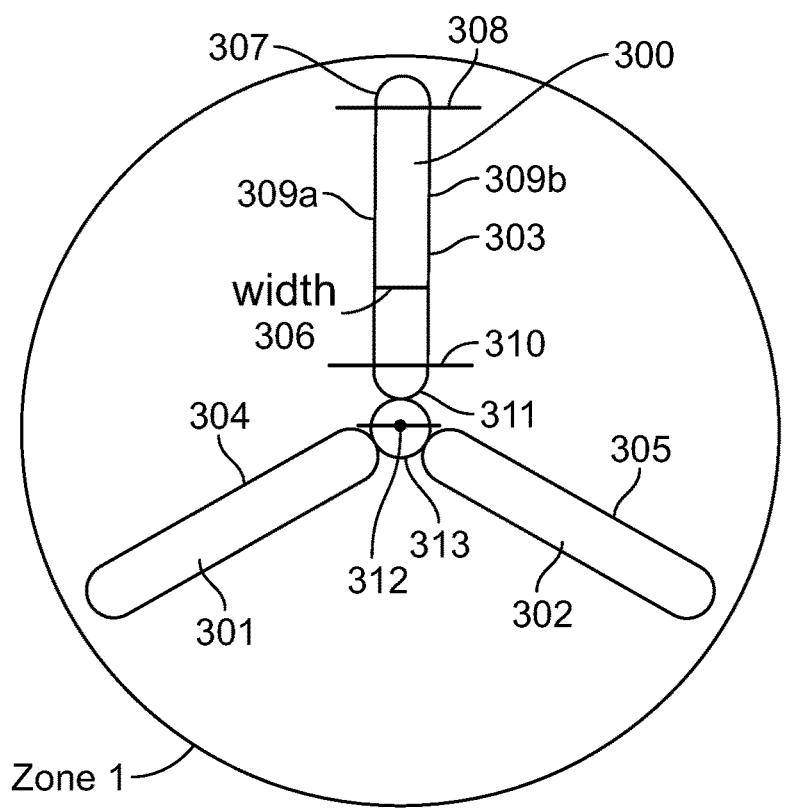
FIG. 3A shows the details of the unit in zone 1.
Figure 3B:
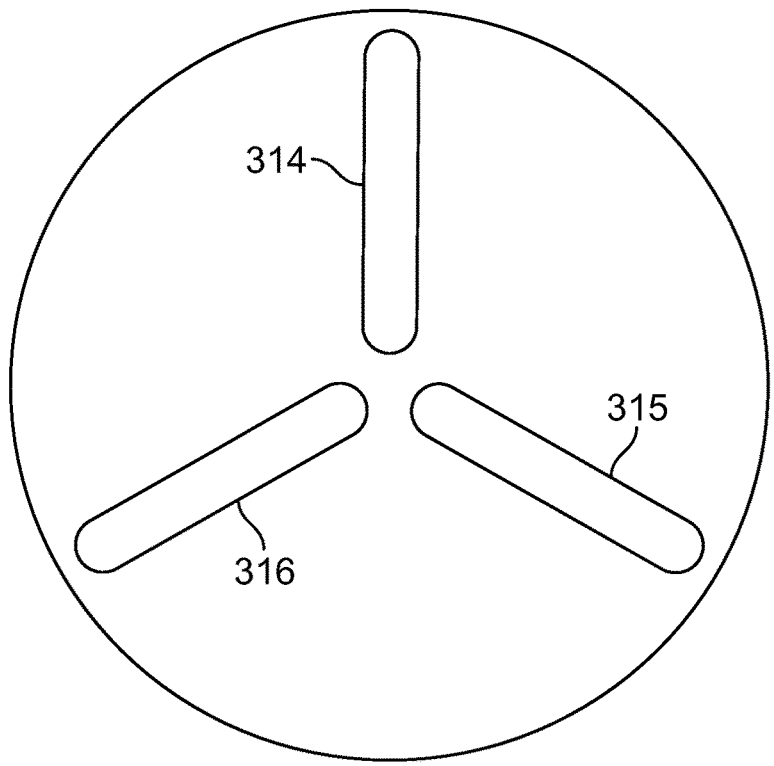
FIG. 3B shows cutout perimeter of the unit in zone 1.

FIGS. 3A, B-9A, B show a close-up image of units from zones 1-7. The units in these figures are shown only as cutout segments, without overlapping units from other zones as is the case when the cutout segments are present in the tube (tube wall). FIG. 3A shows the unit from zone 1 with 3 cutout segments 303, 304 and 305. The cutout segment may be formed by two linear portions 309a, 309b, capped by two curvilinear portions 307 and 311. The curvilinear portions begin at positions 308 and 310, respectively for cutout segment 300. In one embodiment, the width of the cutout 306 divided by 2 equals the radius of the curvilinear portions 307, 311. The open surface area of the cutout segments 303, 304 and 305 is 300, 301 and 302, respectively. In the embodiment shown, the cutout segments, 303, 304 and 305 are positioned equally from the center of symmetry, Cs, 312 by a distance equal to the width 306 divided by 2. In other words, an imaginary circle 313 may be positioned between the cutout segments having a radius equal to the width of the cutout segment 306/2. The cut-pattern perimeter length of the cutout pattern from zone 1 is shown in FIG. 3B and is the sum of perimeters of each of the three cutout segments, 314+315+316.

Figure 4A:
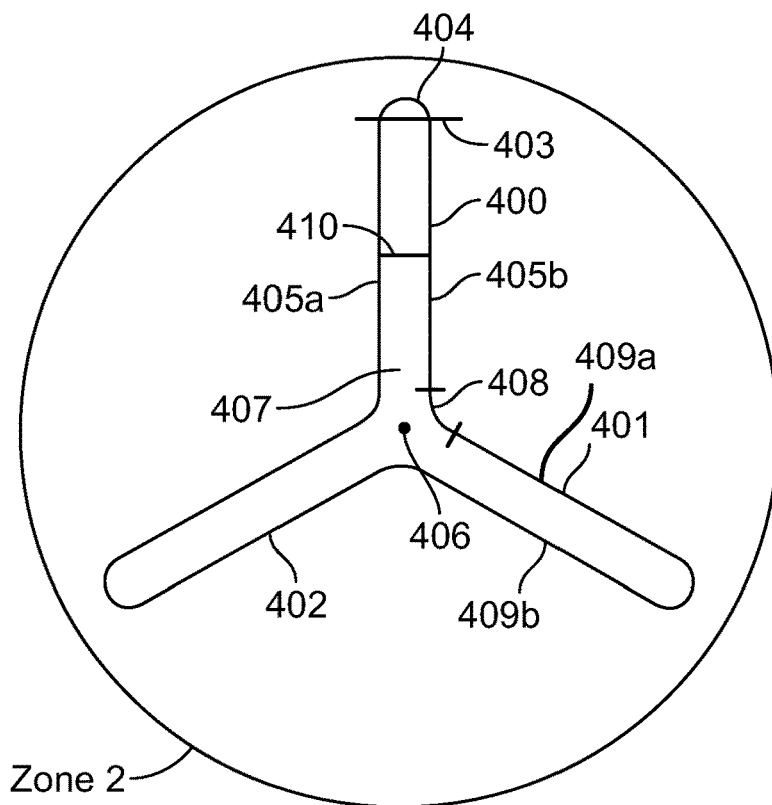
FIG. 4A shows the details of the unit in zone 2.
Figure 4B:
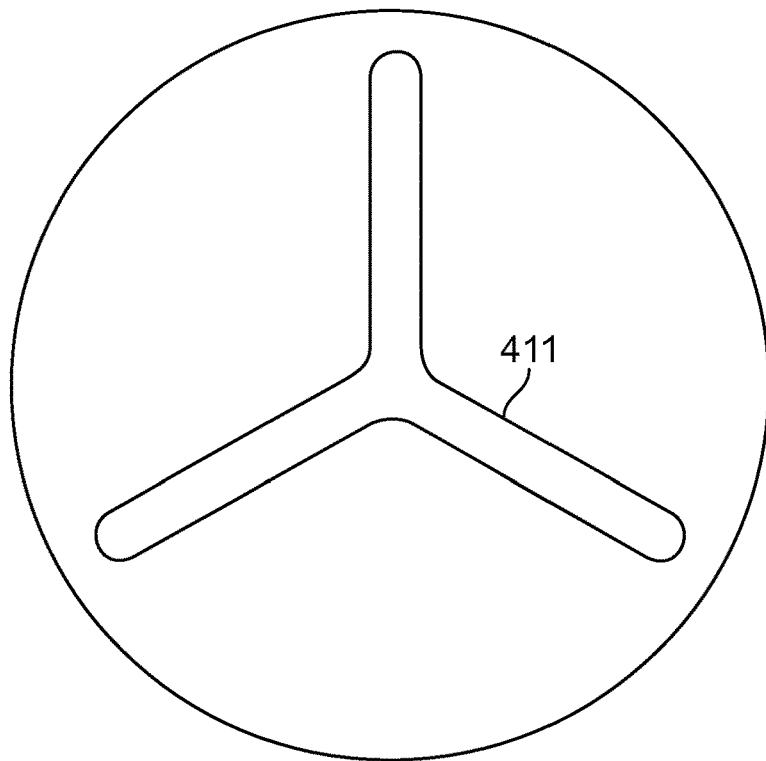
FIG. 4B shows cutout perimeter of the unit in zone 2.

FIG. 4A shows the unit from zone 2. The cutout zone 407 is composed of three contiguous cutout segments 400, 401, 402 which have been merged into a single cutout pattern having an open surface area of 407. Each cutout segment is composed of two, equal linear portions, 405a, 405b, and a curvilinear portion 404 starting at position 403. The center of symmetry, Cs, for the unit is shown as 406. The linear portions of each cutout segment are connected by a curvilinear portion 408; specifically, in the embodiment shown, the linear portion of cutout segment 400, 405b, is connected by a curvilinear portion 408 to the linear portion 409a of the cutout segment 401. The radius of curvature of the curvilinear portions 404 and 408 can vary. The width, i.e., the distance between the two linear portions 405a, 405b can be equal to, less than or greater than the width between the two linear portions shown in zone 1, 306. The cut-pattern perimeter length of the cutout pattern from zone 2 is shown in FIG. 4B and is 411.

Figure 5A:
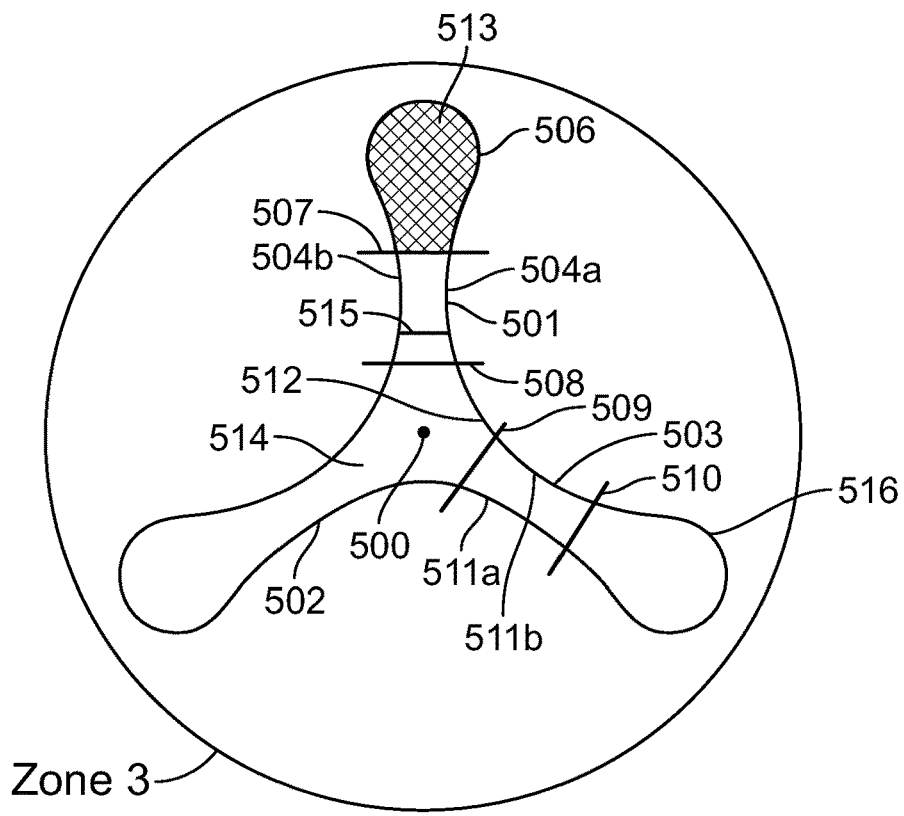
FIG. 5A shows the details of the unit in zone 3.
Figure 5B:
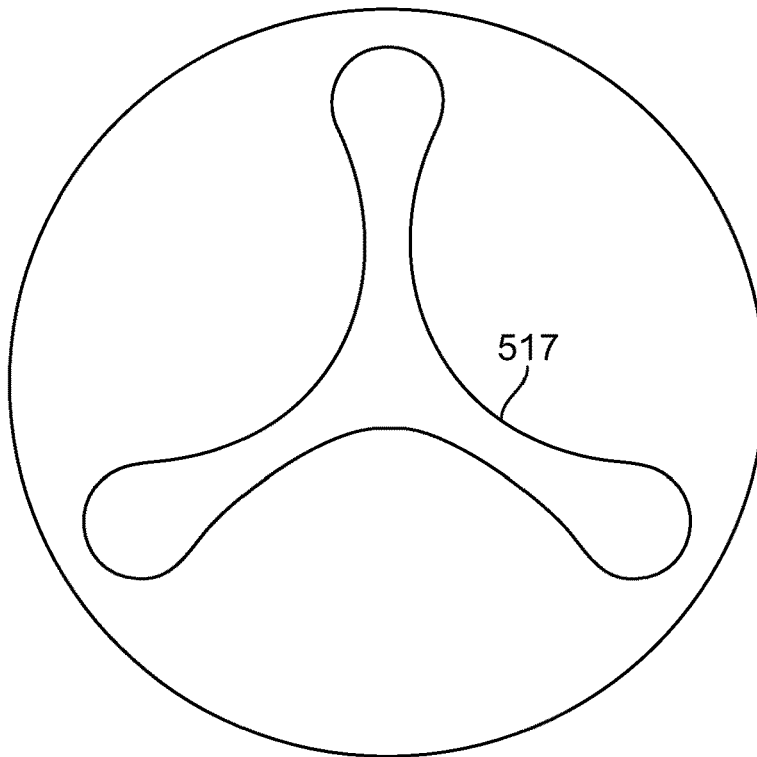
FIG. 5B shows cutout perimeter of the unit in zone 3.

FIG. 5A shows the unit from zone 3. The center of symmetry of the unit is shown as 500 is composed of three contiguous, cutout segments 501, 502, 503 having an open surface area 514. Each cutout segment is composed of two linear portions 504a, 504b, and a curvilinear portion 506, 516 starting at position 507. The open surface area of the curvilinear portion is shown in cross hatch as 513. The shape of the curvilinear portion 506 can vary and only one embodiment is shown in the figure. The cutout segments are connected by a curvilinear portion 512 starting at position 508. As illustrated in the figure, the two equal, linear portions 504a and 511b are connected by a curvilinear portion 512; the degree of curvature of the curvilinear portion 512 can vary. The width of the 515 between the two linear portions 504a, 504b can be equal to, less than or greater than the width of the between the two linear portions 410 in zone 2, FIG. 4a. The length of the linear portions 504a, 504b is less than, equal to or the greater than the linear portions in zone 2, 405a, 405b. In the embodiment shown the linear portions 504a=504b<405a=405b. The cut-pattern perimeter length of the cutout pattern from zone 3 is shown in FIG. 5B and is 517.

Figure 6A:
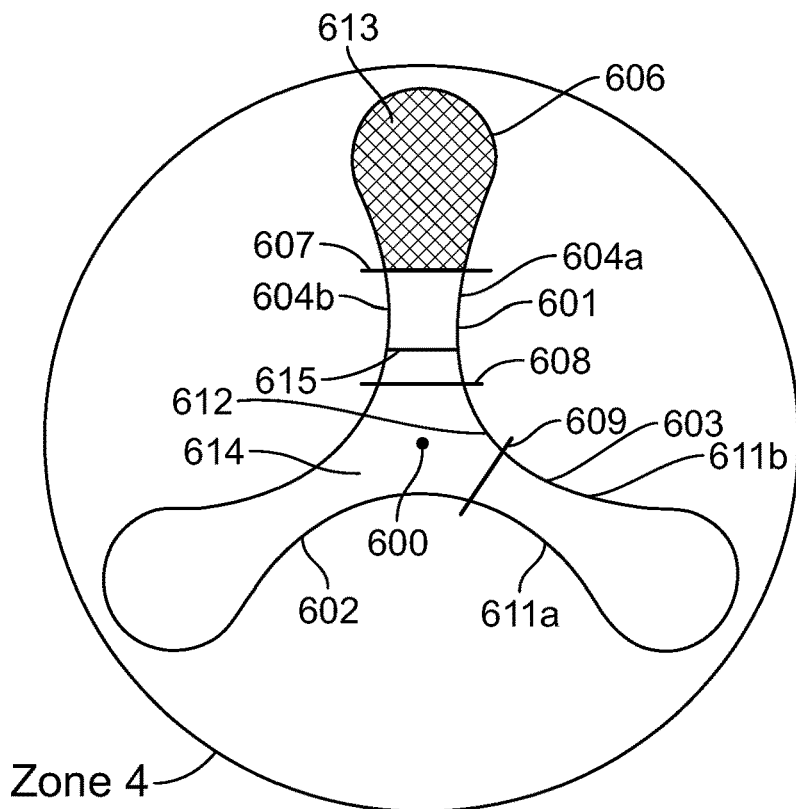
FIG. 6A shows the details of the unit in zone 4.
Figure 6B:
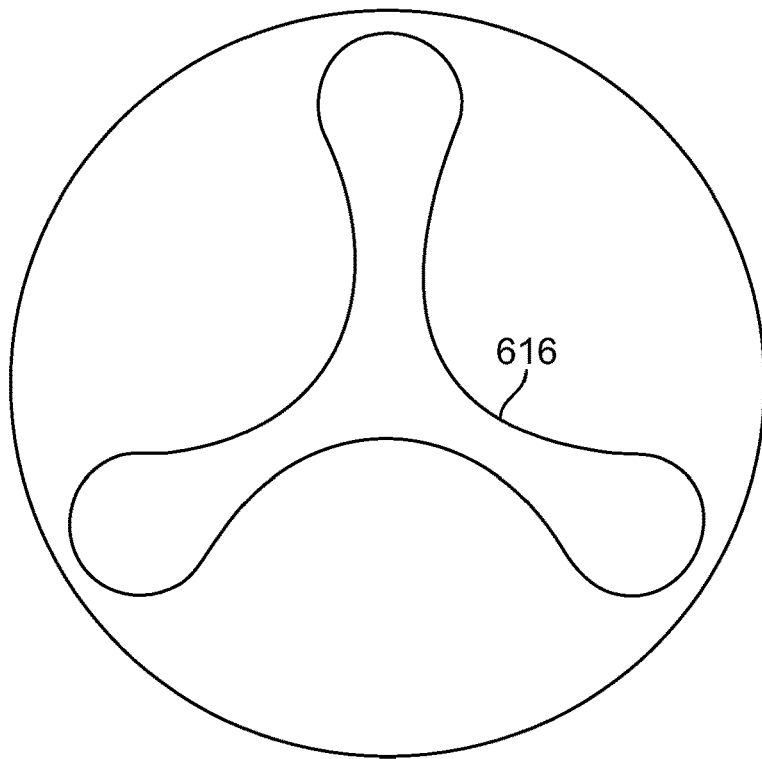
FIG. 6B shows cutout perimeter of the unit in zone 4.

FIG. 6A shows the unit from zone 4. The center of symmetry, Cs, of the unit is shown as 600 is composed of three contiguous, cutout segments 601, 602, 603 having an open surface area 614. Each cutout segment is composed of two linear portions 604a, 604b, and a curvilinear portion 606, starting at position 607. The open surface area of the curvilinear portion is shown in cross hatch as 613. The shape of the curvilinear portion 606 can vary and only one embodiment is shown in the figure. The cutout segments are connected by a curvilinear portion 612 starting at position 608. As illustrated in the figure, the two equal, linear portions 604a and 604b are connected by a curvilinear portion 612; the degree of curvature of the curvilinear portion 612 can vary. The width of the 615 between the two linear portions 604a, 604b can be equal to, less than or greater than the width of the between the two linear portions 515 in zone 3, FIG. 5a. The length of the linear portions 604a, 604b is less than, equal to or the greater than the linear portions in zone 3, 505a, 505b. In the embodiment shown the linear portions 604a=604b<505a=505b. The cut-pattern perimeter length of the cutout pattern from zone 4 is shown in FIG. 6B and is 616.

Figure 7A:
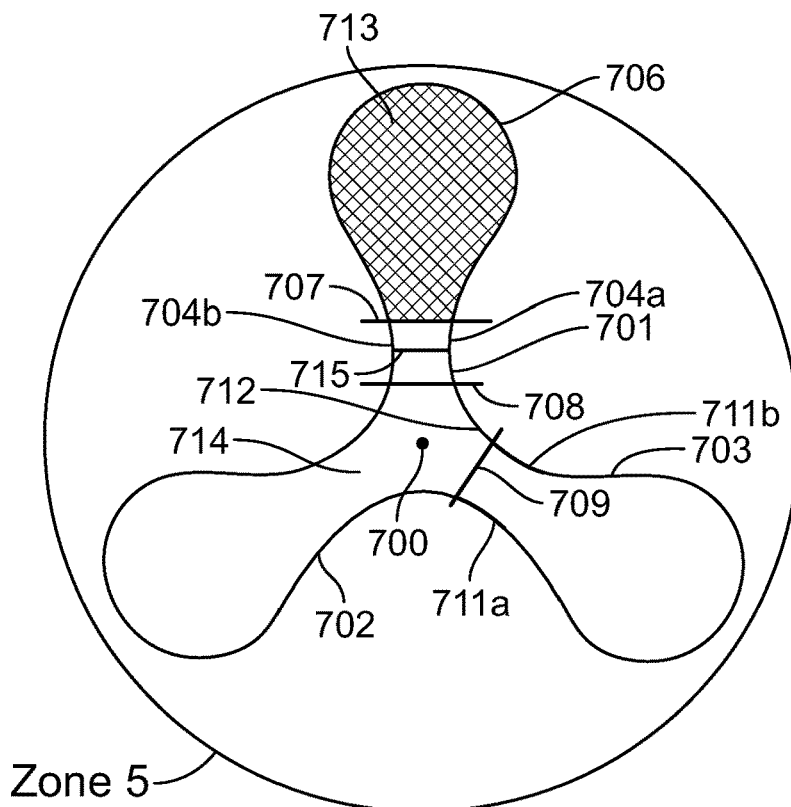
FIG. 7A shows the details of the unit in zone 5.
Figure 7B:
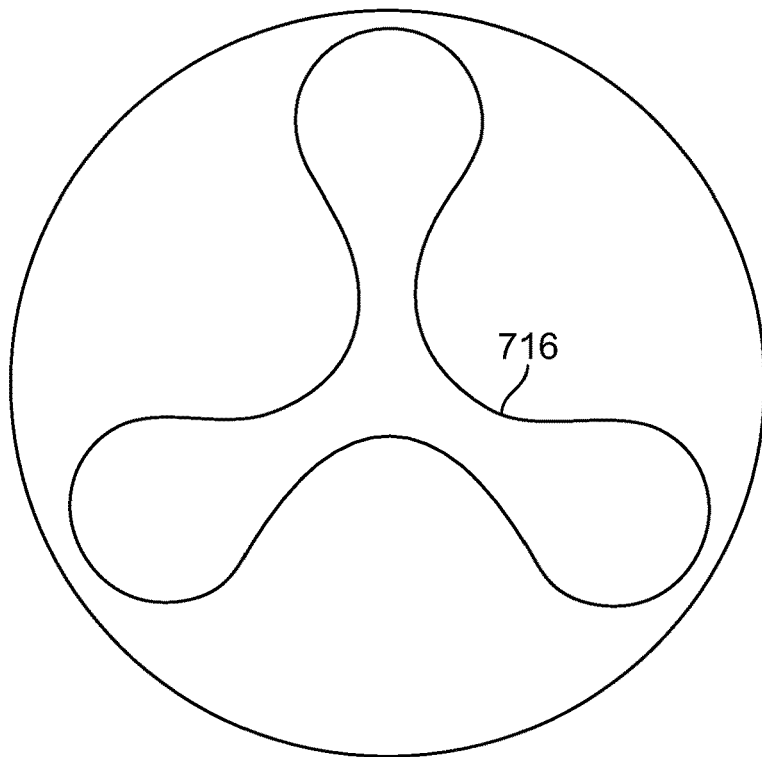
FIG. 7B shows cutout perimeter of the unit in zone 5.

FIG. 7A shows the unit from zone 5. The center of symmetry, Cs, of the unit is shown as 700 is composed of three contiguous, cutout segments 701, 702, 703 having an open surface area 714. Each cutout segment is composed of two linear portions 704a, 704b, and a curvilinear portion 706, starting at position 707. The open surface area of the curvilinear portion is shown in cross hatch as 713. The shape of the curvilinear portion 706 can vary and only one embodiment is shown in the figure. The cutout segments are connected by a curvilinear portion 712 starting at position 708. As illustrated in the figure, the two equal, linear portions 704a and 704b are connected by a curvilinear portion 712; the degree of curvature of the curvilinear portion 712 can vary. The width of the 715 between the two linear portions 704a, 704b can be equal to, less than or greater than the width of the between the two linear portions 615 in zone 4, FIG. 6a. The length of the linear portions 704a, 704b is less than, equal to or the greater than the linear portions in zone 4, 605a, 605b. In the embodiment shown the linear portions 704a=704b<605a=605b. The cut-pattern perimeter length of the cutout pattern from zone 5 is shown in FIG. 7B and is 716.

Figure 8A:
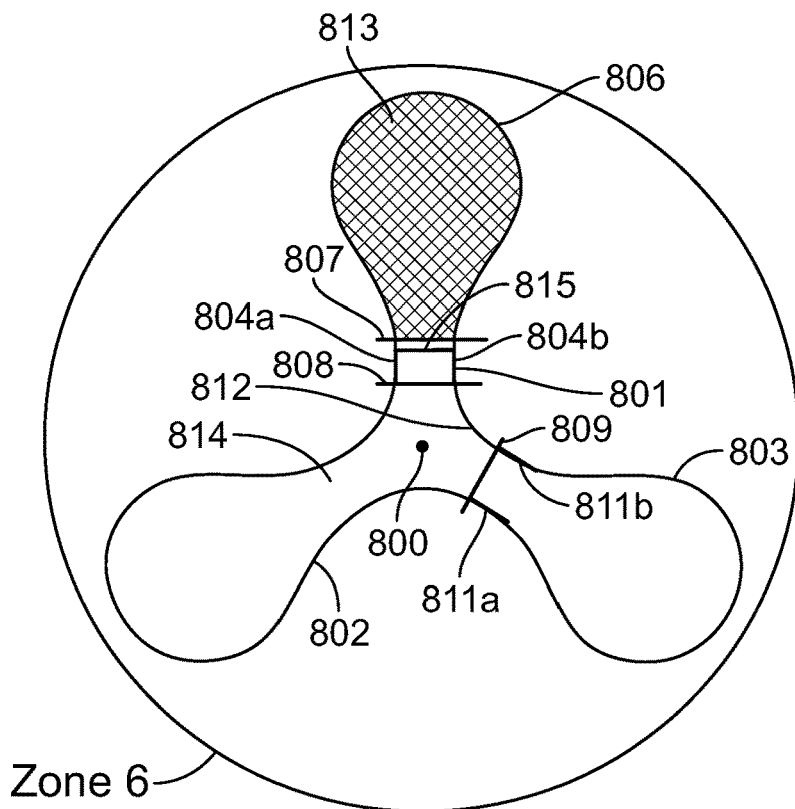
FIG. 8A shows the details of the unit in zone 6.
Figure 8B:
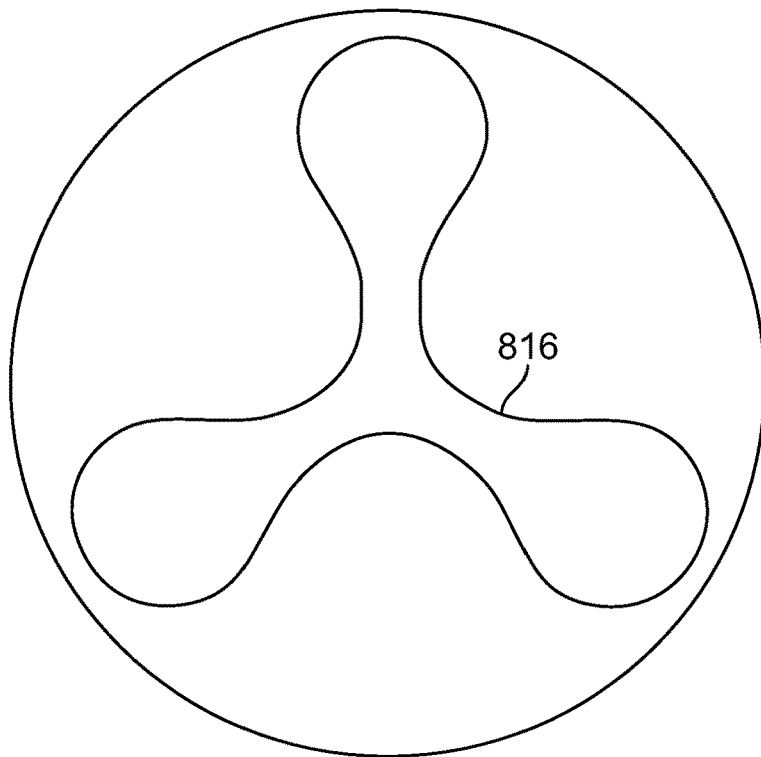
FIG. 8B shows cutout perimeter of the unit in zone 6.

FIG. 8A shows the unit from zone 6. The center of symmetry, Cs, of the unit is shown as 800 is composed of three contiguous, cutout segments 801, 802, 803 having an open surface area 814. Each cutout segment is composed of two linear portions 804a, 804b, and a curvilinear portion 806, starting at position 807. The open surface area of the curvilinear portion is shown in cross hatch as 813. The shape of the curvilinear portion 706 can vary and only one embodiment is shown in the figure. The cutout segments are connected by a curvilinear portion 812 starting at position 808. As illustrated in the figure, the two equal, linear portions 804a and 804b are connected by a curvilinear portion 712; the degree of curvature of the curvilinear portion 712 can vary. The width of the 815 between the two linear portions 804a, 804b can be equal to, less than or greater than the width of the between the two linear portions 715 in zone 5, FIG. 7a. The length of the linear portions 804a, 804b is less than, equal to or the greater than the linear portions in zone 5, 705a, 705b. In the embodiment shown the linear portions 804a=804b<705a=705b. The cut-pattern perimeter length of the cutout pattern from zone 6 is shown in FIG. 8B and is 816.

Figure 9A:
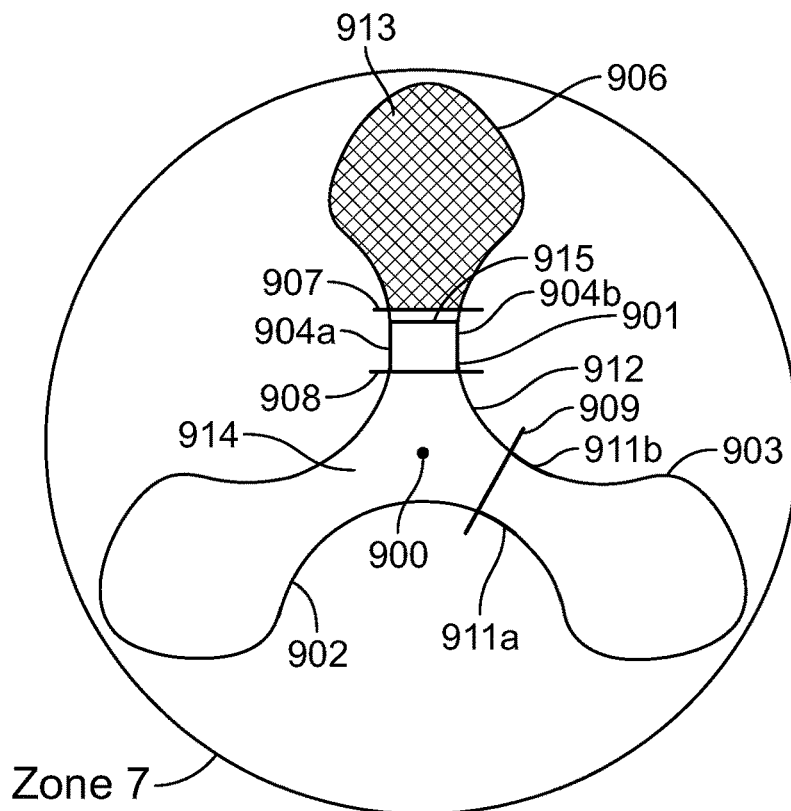
FIG. 9A shows the details of the unit in zone 7.
Figure 9B:
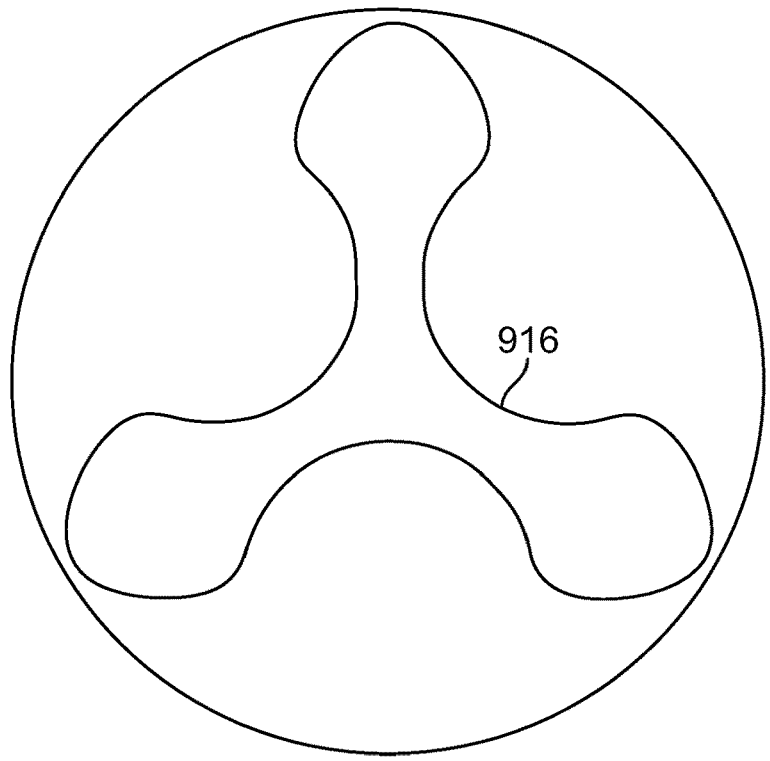
FIG. 9B shows cutout perimeter of the unit in zone 7.
Figure 10D:
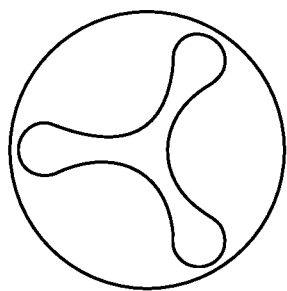
FIG. 10A-10H show the transition across zones 1 to 7.
Figure 10C:
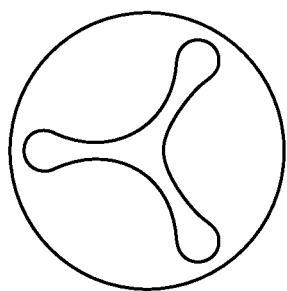
Figure 10B:
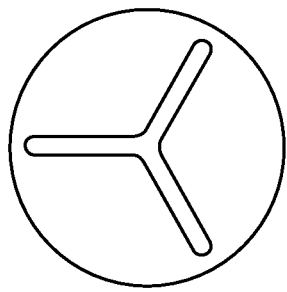
Figure 10A:
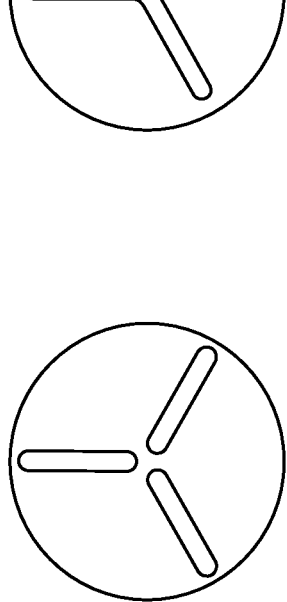
Figure 10G:
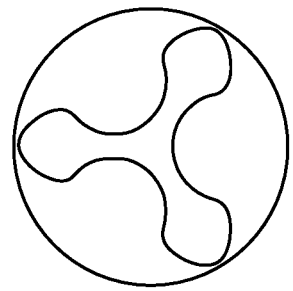
Figure 10F:
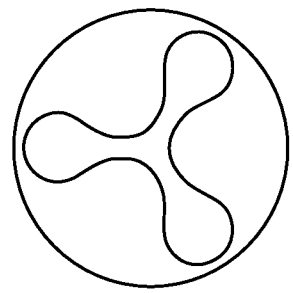
Figure 10E:
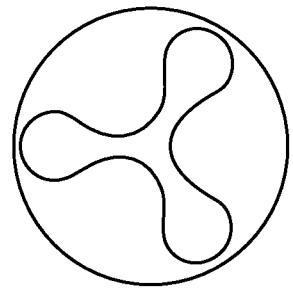
Figure 10H:
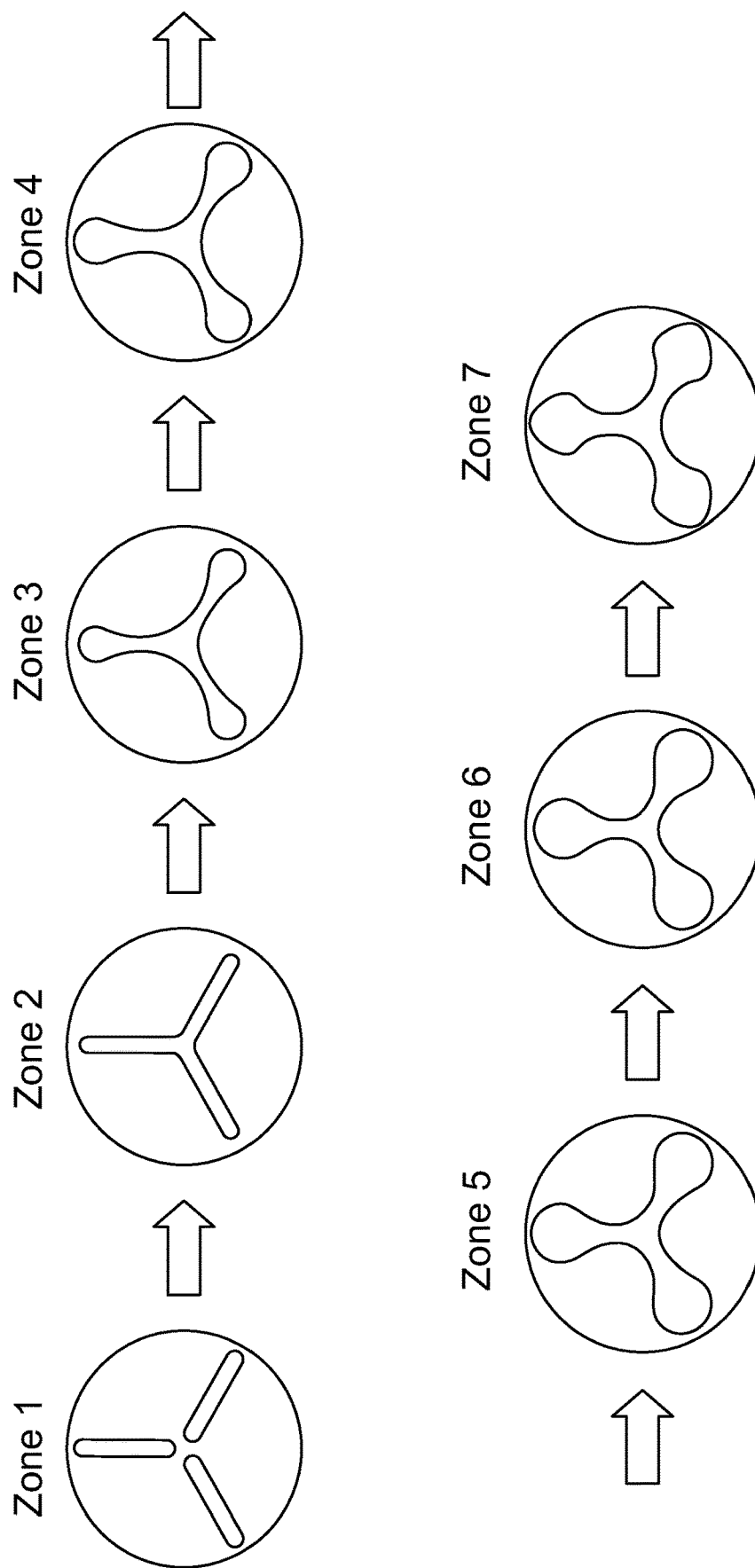

FIG. 9 shows the unit from zone 7. The center of symmetry, Cs, of the unit is shown as 900 is composed of three contiguous, cutout segments 901, 902, 903 having an open surface area 914. Each cutout segment is composed of two linear portions 904a, 904b, and a curvilinear portion 906, starting at position 907. The open surface area of the curvilinear portion is shown as a cross hatch 913. The shape of the curvilinear portion 906 can vary and only one embodiment is shown in the figure. The cutout segments are connected by a curvilinear portion 912 starting at position 908. As illustrated in the figure, the two equal, linear portions 904a and 911b are connected by a curvilinear portion 912; the degree of curvature of the curvilinear portion 912 can vary. The width of the 915 between the two linear portions 904a, 904b can be equal to, less than or greater than the width of the between the two linear portions 815 in zone 6, FIG. 8a. The length of the linear portions 904a, 904b is less than, equal to or the greater than the linear portions in zone 6, 805a, 805b. In the embodiment shown the linear portions 904a=904b<805a=805b. The cut-pattern perimeter length of the cutout pattern from zone 7 is shown in FIG. 9B and is 916.

An overview of the transition of the units across zone 1 to zone 7 is shown in FIGS. 10A-10H. The following characteristics apply to the dimensions across the zones. The open surface area of the cutout areas across the different zones rank orders as: (300+301+302)<407<514<614<714<814<914. The rank order of the open surface area of the curvilinear portion is: 513<613<713<813<913. The rank of the linear portions is: 904a=904b<805a=805b<704a=704b<605a=605b<505a=505b. The rank order of the cut-pattern perimeter lengths is (314+315+316)<411<517<616<716<816<916. The change in either open surface area or cut-pattern perimeter length across multiple zones can be linear, exponential, assume a step-wise or square wave function and be increasing, decreasing, constant, continuous or discontinuous.

Within any one zone, the cutout segments forming a unit may assume any symmetrical shape about a center of symmetry, Cs. There may be 1, 2, 3, 4, 5, 6, 7, 8, 9, 10 or n cutout segments in a unit. The cutout segments may be continuous or separate. For example, the cutout segment may form a circle or a symmetrical, n-sided polygon, such as a hexagon or octagon. Different zones may have the same or different symmetrical shapes. The geometric rules, both within a zone as well as across a zone remain the same in these embodiments as they are for the triplex cutout segments described above. Specifically, the units are arranged in a band. A band or row can have 2, 3, 4, 5, 6, 7, 8, 9, 10, 20, 30, 40, 50, 60, 70, 80, 90, 100, 200, 300, 400, 500, 1000 to n units. The spacing between units in a band represented as dc, where dc is the distance between the center of symmetry, Cs, of two adjacent units in a band, dc, is equal within a single band and may be constant across the length of the tube in different zones. The spacing between bands within a zone and across zones may be equal as well. All cutout segments of the units within a zone can have the same orientation or are in-phase with respect to the line through the center of symmetry for each row or band. The cutout segments in adjacent bands or rows within a zone can also have the same orientation or are in-phase with respect to the line through the center of symmetry for each row. The center of symmetry, Cs, of units within the same zone, but in adjacent bands is shifted. Between two adjacent zones, the units are shifted around the circumference of the band such that a straight line can be drawn between the center of symmetry for units in adjacent zones. The center of symmetry, Cs, in different bands falls along the same line in every other band. In other words, the center of symmetry of each unit is positioned at the same point on the circumference of the tube as the center of symmetry of a second unit in a third, third, fifth, etc. band which is separated by one band from the first band.

One tube may contain multiple zones. For example, the tube can be provided with 1, 2, 3, 4, 5, 6, 7, 8, 9, 10, 11, 12, 13, 14 or 15 (higher numbers are also possible, e.g. 20, 30, 40, 50, 60, 70, 80, 90, 100, 200, 300, 400, 500, 600, 700, 800, 900, 1000 to n different zones). If a tube contains multiple zones, then across different zones there may be a change in open surface area and cut-pattern perimeter length. For example, if the cutout segment is formed in the shape of a hexagon and there are seven zones, a first zone, a second zone, a third zone, a fourth zone, a fifth zone, a sixth zone and a seventh zone, then the rank order for the open surface area and cut-pattern perimeter length is: unit of first zone<unit of second zone<unit of third zone<unit of fourth zone<unit of fifth zone<unit sixth zone. If there are equal number of units per zone, then the rank order applies to zones as well. The change in either open surface area or cut-pattern perimeter length across multiple different zones can be linear, exponential or assume a step-wise or square wave function and be increasing, decreasing, constant, continuous or discontinuous.

In embodiments formed from other cutout segments, e.g., circles or n-sided polygons, the width across any uncut portion, may be varied, i.e., the width may be reduced. This reduction in width will result in an increase in the open surface area 1004. By increasing the open surface area, the uncut surface area within unit in any one zone, the flexibility of that portion composed of such units with increased open surface area of the cutout segments will increase.

Figure 11B:
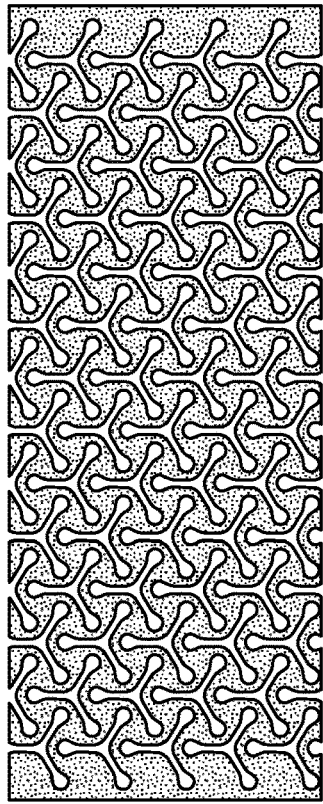
FIG. 11B shows the cutout for a tube composed of zone 3.
Figure 11A:
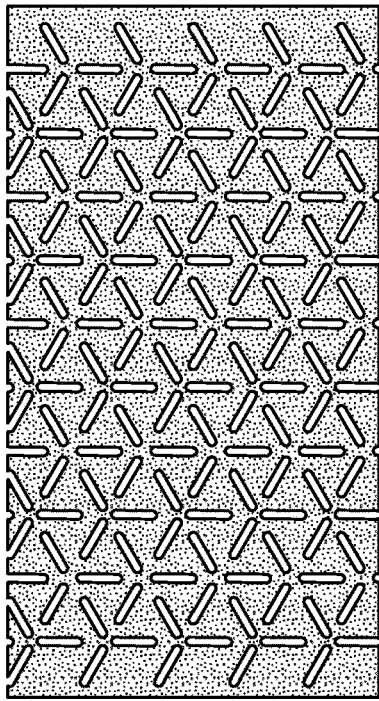
FIG. 11A shows the cutout for a tube composed of zone 1.
Figure 11D:
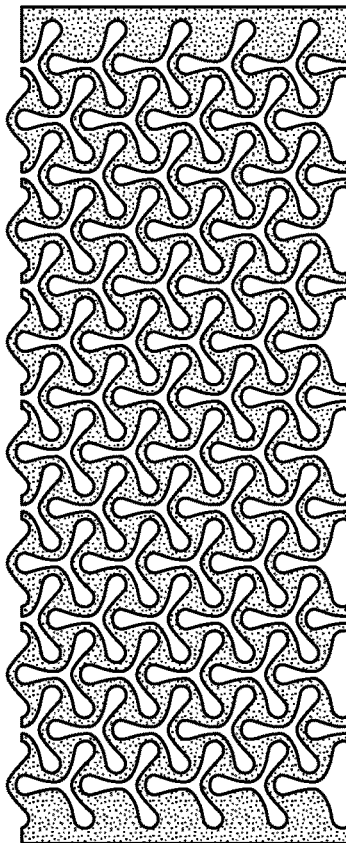
FIG. 11D shows the cutout for a tube composed of zone 5.
Figure 11C:
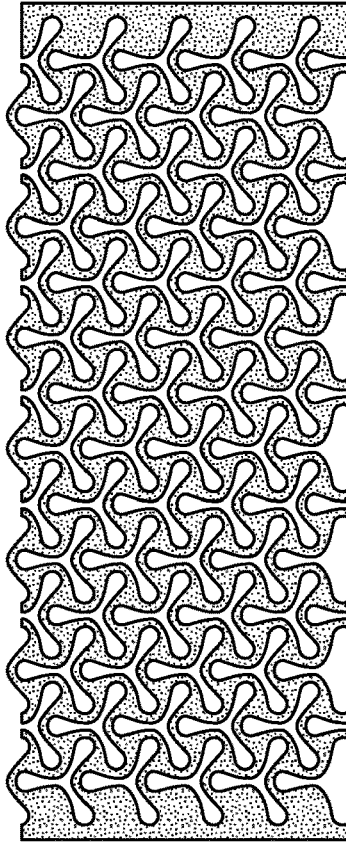
FIG. 11C shows the cutout for a tube composed of zone 4.
Figure 11E:
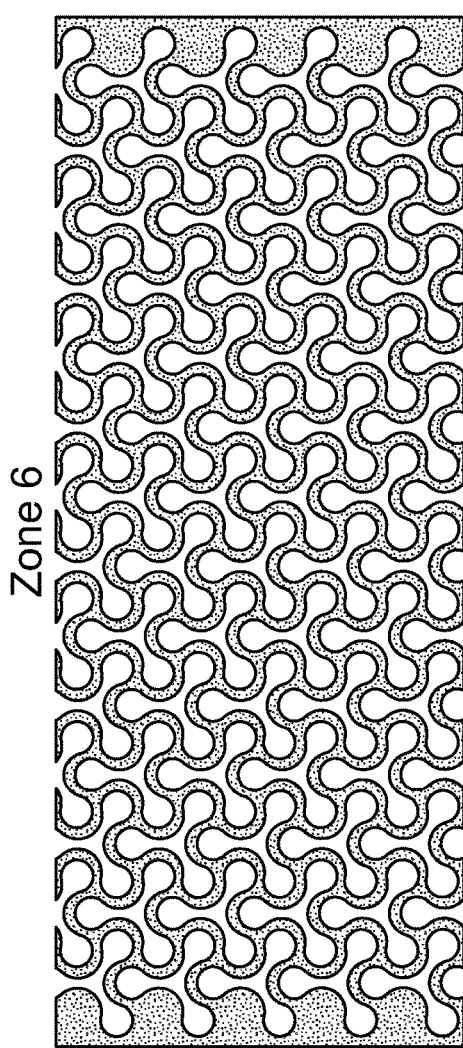
FIG. 11E shows the cutout for a tube composed of zone 6.

The portion of the tube wall remaining after the cutout segments are removed may vary across the length of the tube and is inversely correlated with the open surface area of the cutouts. This inverse correlation is evident from FIGS. 11A-11E which show the cutout patterns of units, white or unmarked, contrasted with the remaining uncut surface of the tube, shown in dark color, e.g., black, with stippling. The zones are labeled as followed: zone 1, FIG. 11A, zone 3, FIG. 11B, zone 4, FIG. 11C, zone 5, FIG. 11D and zone 6, FIG. 11E. As is evident from the figures, the remaining dark color, e.g., black with stippling or uncut material in the wall of the tube decreases as the open surface area of the cutout areas in the unit increases, i.e., the uncut area is inversely correlated with the cutout surface areas. The flexibility of the tube may be precisely controlled at any position along the tube by combining one or more zones at various positions along the length of the tube. Flexibility of the tube is positively correlated with the open surface area. In other words, as the open surface area of a cutout segment increases the flexibility of a zone composed of units having the larger cutout segments increases. Conversely, flexibility is inversely correlated with the uncut area; as the uncut surface area increases, flexibility decreases.

When zones are combined there may be a continuous transition in the remaining uncut area as shown in black across the various zones. The total uncut area at any one point on the tube will depend on a number of factors, including the number of bands in each zone and the dimensions of the cutout segments (the open surface area of a particular unit). If the number of bands in each zone are constant, then the rank order is for the uncut surface area, unit of zone 1>unit of zone 2>unit of zone 3>unit of zone 4>unit of zone 5>unit of zone 6>unit of zone 7 (in other words, there is a fading of uncut area across zones) and the rank order of flexibility of the tube is zone 1<zone 2<zone 3<zone 4<zone 5<zone 6<zone 7 (flexibility is positively correlated with the open surface area and inversely correlated with the uncut area). The change in flexibility across multiple different zones can be linear, exponential or assume a step-wise or square wave function, increasing, decreasing, constant, discontinuous or continuous.

Figure 11F:
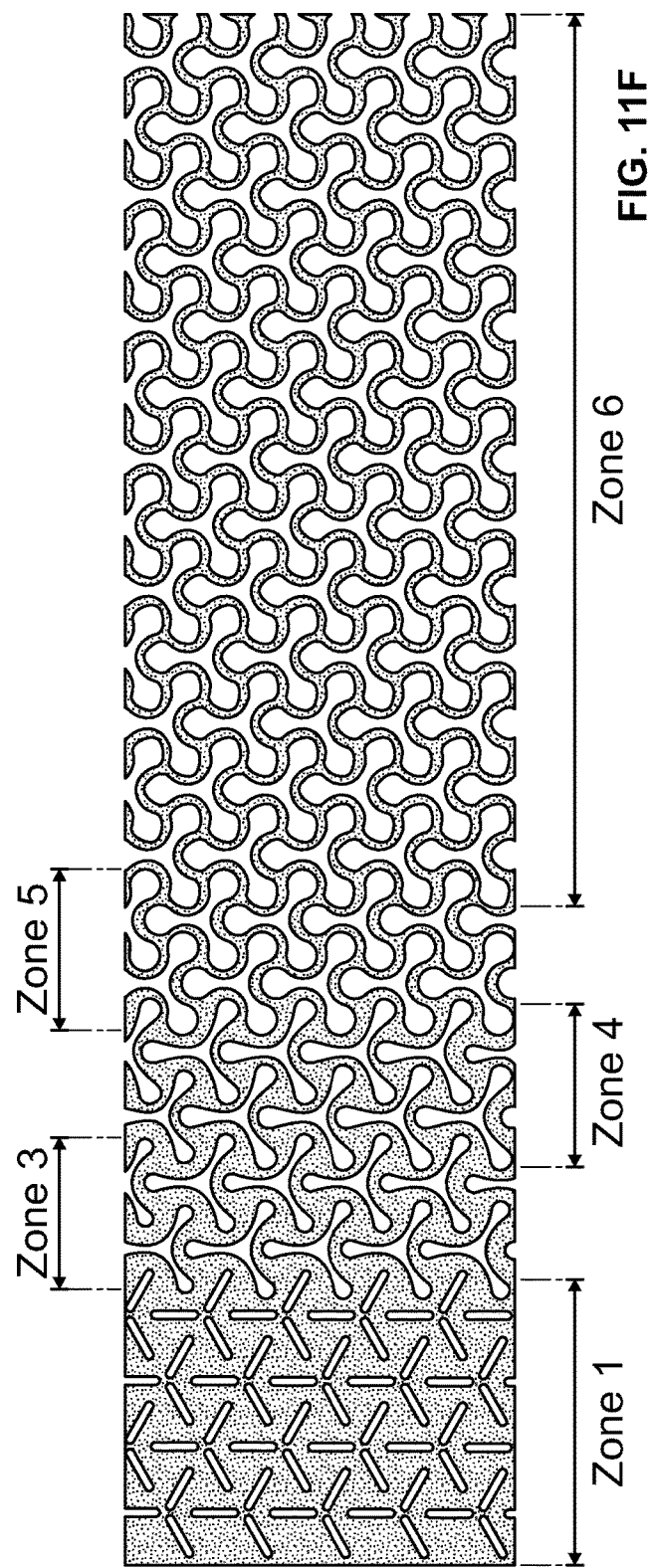
FIG. 11F shows the cutout for tube composed of zones 1, 3, 5, 5 and 6.

One embodiment where the number of bands of units in each zone are not the same is shown in FIG. 11F.

Figure 12A:
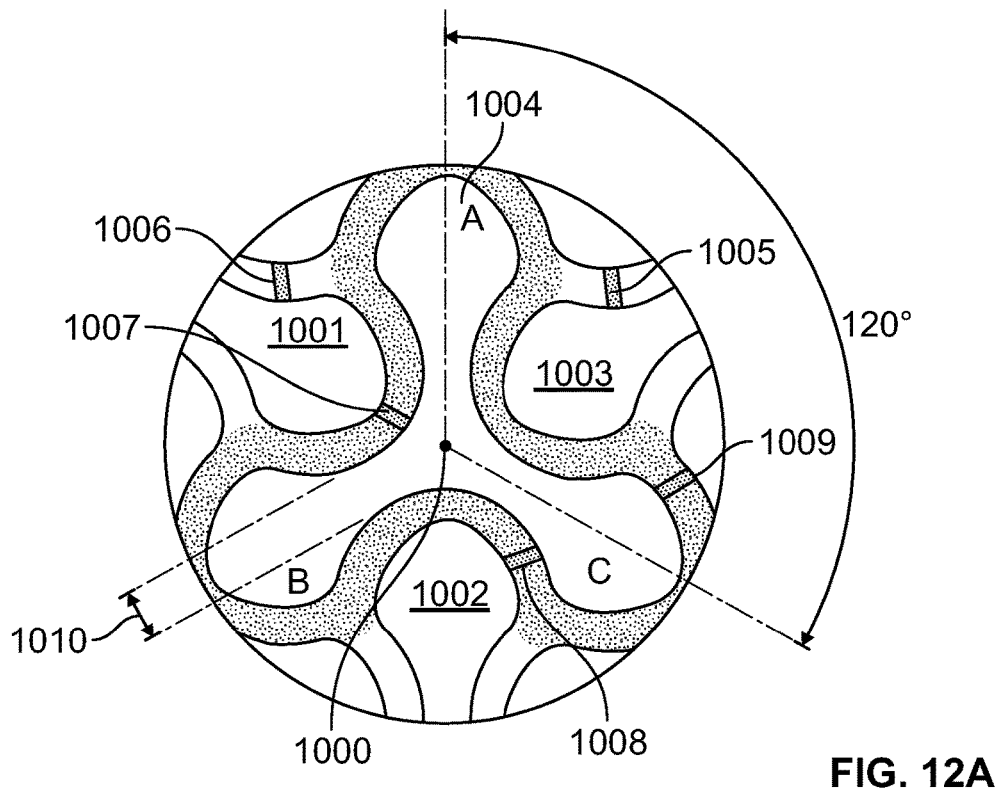
FIG. 12A shows further details for the unit of zone 7.
Figure 12B:
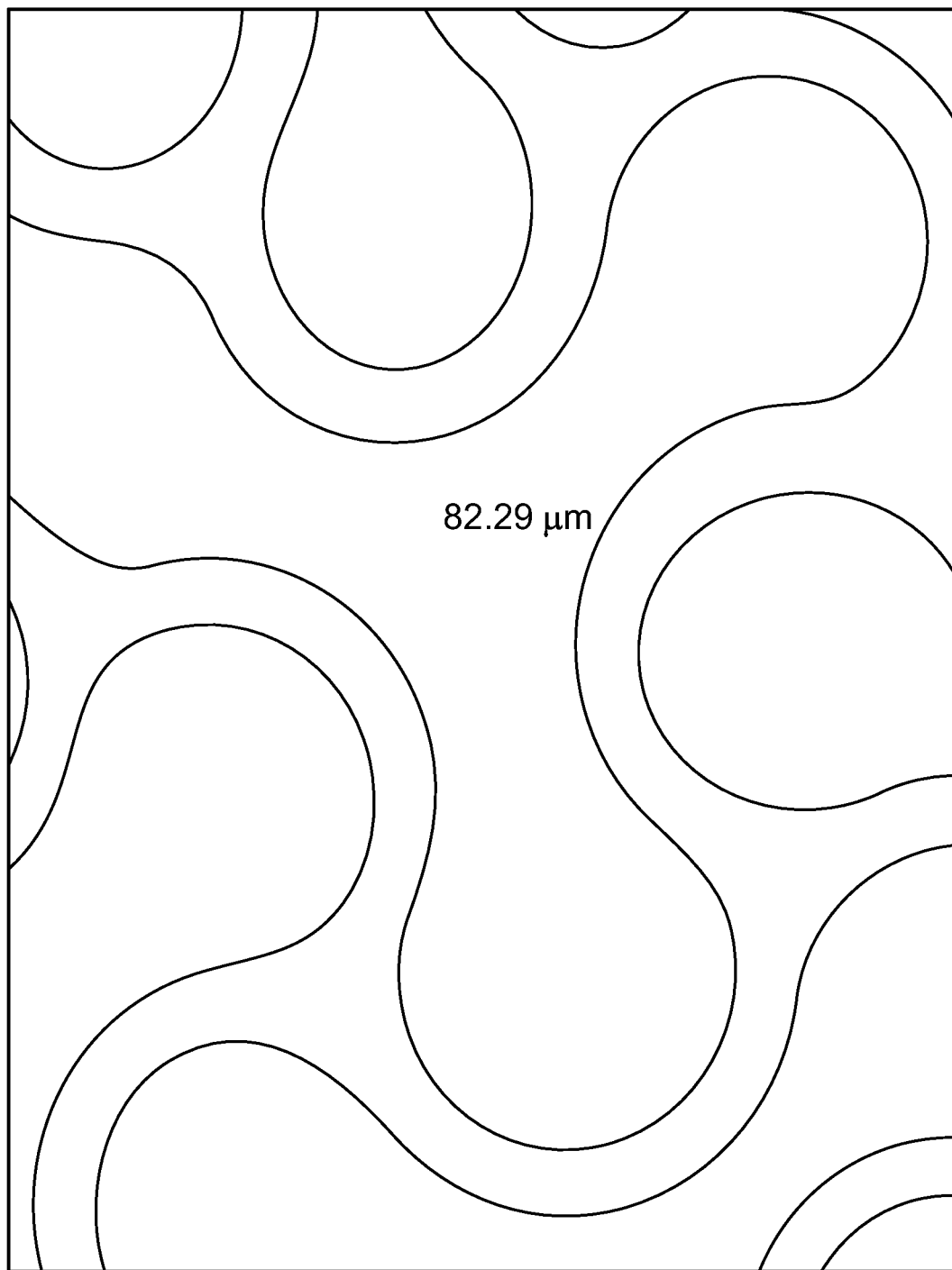
FIGS. 12B, 12C show photomicrographs with a reduction in width (strut width) from 10%, and 50%, respectively.
Figure 12C:
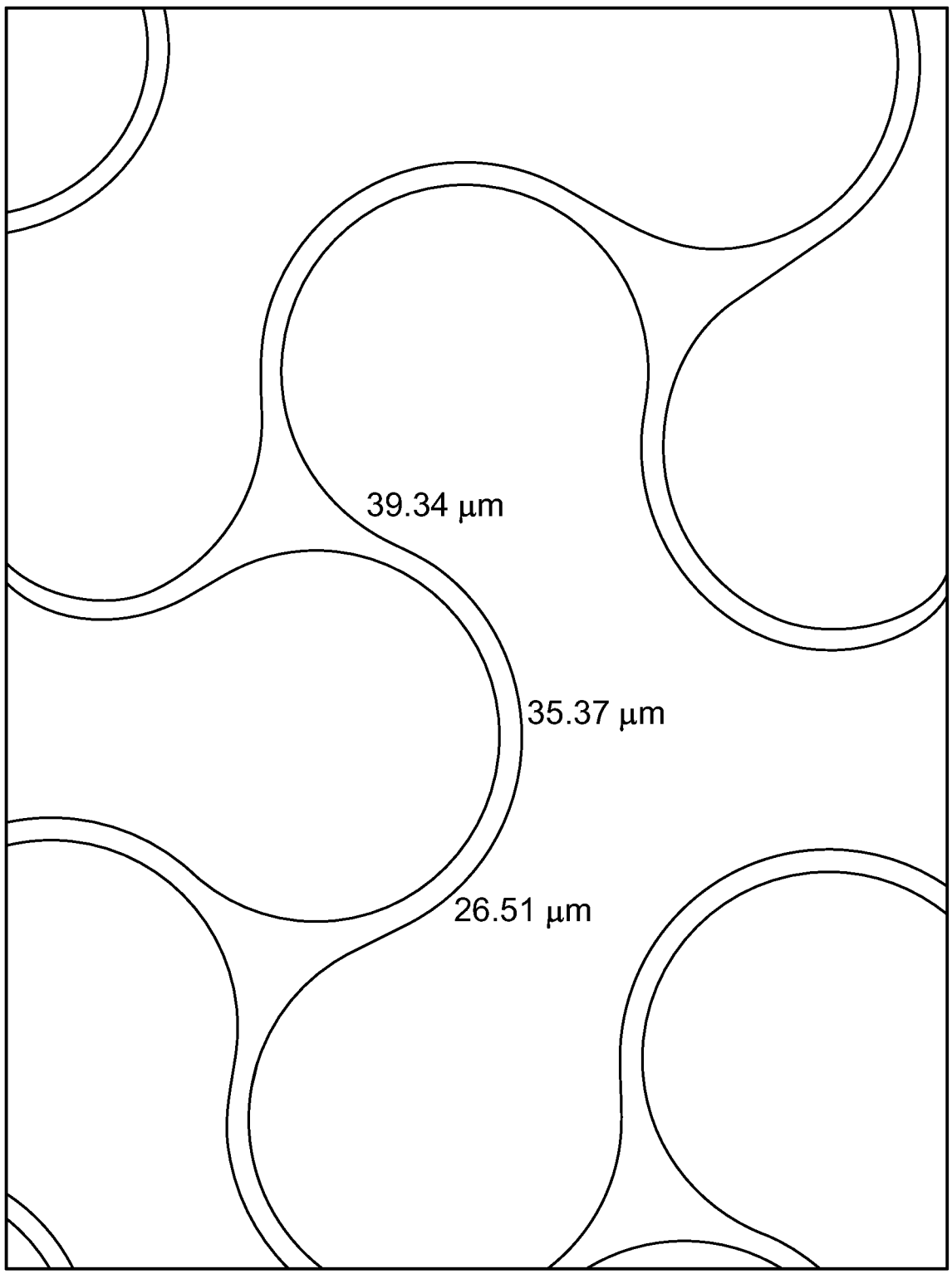

A unit in zone 7 is shown in FIG. 12A. The uncut area of the segment in the unit of zone 7 in FIG. 12 is shown in stripes. In zone 7, the open surface area 1004 of the cutout segment may be increased as follows. The center of symmetry for the cutout segments comprising A, B, C is 1000. The figure shows portions of three other units from zone 7, 1001, 1002, and 1003. The width across any uncut portion, 1005, 1006, 1007, 1008, 1009 (shown only as sample points) may be varied, i.e., the width may be reduced. In one embodiment, the width 1005, 1006, 1007, 1008, 1009 may be equal. The width 1005, 1006, 1007, 1008, 1009 may be further reduced in a uniform or non-uniform manner. This reduction in width will result in an increase in 1010 with a corresponding increase in the open surface area 1004. By increasing the open surface area, the uncut surface area within a unit in zone 7, the flexibility of that portion composed of such units with increased open surface area of the cutout segments will increase. FIGS. 12B and 12C show photomicrographs with a reduction in width of the uncut surface area or strut wall from 10% and 50%, respectively (the dimensions are show in micrometers, μM at the bars shown in the figures). In other embodiments, the reduction in width can be applied to any zone to increase the open surface area within one zone or across multiple zones, thereby altering flexibility.

The cutout segment patterns described here can be applied to a variety of flexible shaft devices, to replace, supplement or be combined with braiding and coil composite configurations with a single thin walled frame. By using different zone patterns along the shaft length, flexibility can be increased or decreased along the shaft length, as well as other characteristics of the tube, such as torque, flexibility, pushability, resistance to axial compression and stretch, maintaining lumen diameter and kink resistance.

Figure 13:
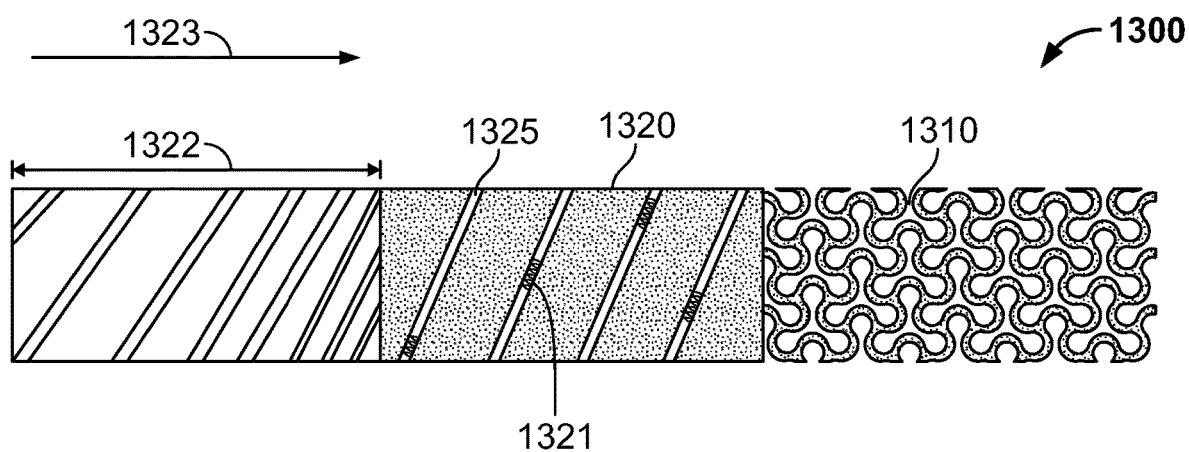
FIG. 13 is an unrolled plan view of a tube having hybrid cut patterns including a spiral cut section and a section having a triplex cut pattern, according to one embodiment of the present invention.

The cutout segment patterns described here, as well as other cut features of the tube can be made by techniques commonly known in the art, e.g., by a solid-state, femtosecond laser cutting. The tube portion to be cut can be loaded on a mandrel and the relative movement between the laser beam and the tube portion can be controlled by a computer with pre-programmed with instructions to produce any desired cut patterns. Other material removal techniques commonly known would also include photo-etching, other laser platforms and electrical discharge machining (EDM), According to embodiments of the present invention, and as shown in FIG. 13, a tube 1300 can include a section 1310 that contains one or more zones of the triplex cut patterns described above, as well as a further section 1320 that contain other cut patterns, e.g., a spiral cut-pattern 1325. The spiral cut section may be longer, equal to or shorter than the triplex cut patterns. The spiral cut section 1320 may include several sub-sections that may have different spiral parameters, such as cut widths, gaps, pitches, etc., such that the bending flexibility along the spiral cut section can vary longitudinally as desired. Additionally, the spiral cut section may also include interrupted spiral cuts 1321 where the spiral cuts do not form continuous spirals along the tube wall. The spiral and interrupted spiral cut patterns are also described in co-pending U.S. application Ser. No. 14/854, 242, the disclosure of which is incorporated herein by reference in its entirety. Either or both of the spiral cut section and the triplex section can be encapsulated within an outer jacket and/or an inner lining. The spiral cut may be made using a laser, e.g., femto-second solid-state cutting laser, by removing tube material from the tube wall. A tube portion fabricated with spiral cuts can also be viewed as a ribbon or flat coil (made of portions of the remaining tube wall) wound helically about the longitudinal axis.

The tube may have several different spiral-cut patterns, including continuous and discontinuous. The spiral-cut sections may provide for a graduated transition in bending flexibility. For example, the spiral-cut-pattern may have a pitch that changes the width of the spiral cut ribbon, to increase flexibility in one or more areas. The pitch of the spiral cuts can be measured by the distance between points at the same radial position in two adjacent threads. In one embodiment, the pitch may increase as the spiral cut progresses from a proximal position to the distal end of the catheter. In another embodiment, the pitch may decrease as the spiral cut progresses from a proximal position of the catheter to the distal end of the catheter. In this case, the distal end of the catheter may be more flexible. By adjusting the pitch of the spiral cuts, the pushability, kink resistance, torque, flexibility and compression resistance of the catheter may be adjusted.

Spiral-cut sections having different cut patterns may be distributed along any portion of the length of the tube. The spiral-cut patterns may be continuous (contiguous) or discontinuous along the length of the tube. For example, there may be 1, 2, 3, 4, 5, 6, 7, . . . , n spiral-cut sections along the length of the tube, wherein within each section a constant cut-pattern may be present but across different sections the cut patterns vary, e.g., in terms of pitch. Each section may also contain a variable pitch pattern within the particular section. Each spiral-cut section may have a constant pitch, e.g., in the range of from about 0.05 mm to about 10 mm, e.g., 0.1 mm, 0.2 mm, 0.3 mm, 0.4 mm, 0.5 mm, 0.6 mm, 0.7 mm, 0.8 mm, 0.9 mm, 1.0 mm, 1.5 mm, 2.0 mm, 3.0 mm, 3.5 mm, 4.0 mm, etc. The pitch may also vary within each section. The pitches for different spiral-cut sections may be same or different. Alternatively, the tube may have a continuously changing spiral-cut-pattern along the length of the tube. The orientation or handedness of spiral-cut sections in the tube may also vary among spiral-cut sections. Similar to what has been described with respect to continuous spiral-cuts herein, an interrupted spiral-cut-pattern can also have a varying pitch that decreases from a relatively rigid region to a relatively flexible region.

Figure 14A:
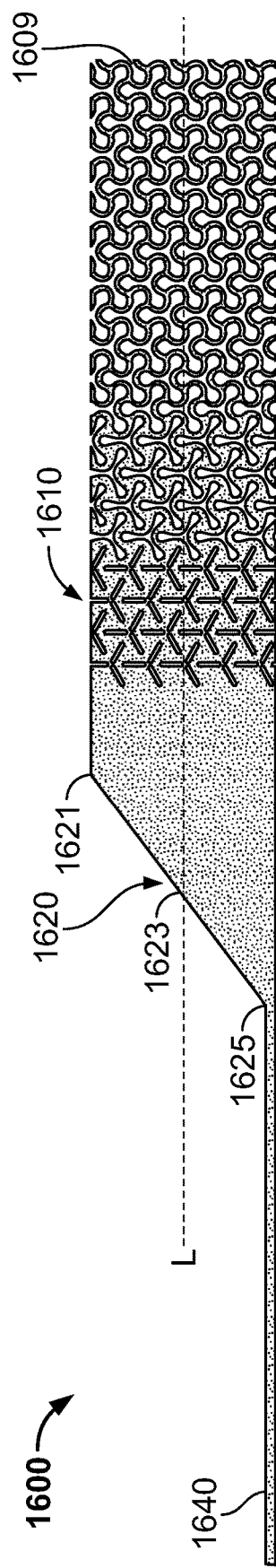
FIG. 14A is a side cross sectional view of a portion of a guide catheter extension including multiple triplex pattern zones according to one embodiment of the present invention.

A tube with triplex cut patterns as described here can be used as a portion of a medical device, e.g., a catheter (which can also be referred to as a guide catheter extension). One embodiment, of the tube which is incorporated into the catheter is shown in FIG. 14. As schematically shown in FIG. 14A, a catheter 1600 (more particularly, a guide catheter extension) can include a tube portion 1610 (a distal tube portion) having multiple zones of triplex patterns of varying surface area coverage as described above, a skived (angled entrance port) collar transition section 1620 adjacent the distal tube portion 1610 and having a tapered edge, the taper having a short end 1621 (closest to the distal tip 1609 of the catheter) and a long end 1625 (furthest away from the distal tip 1609), a push rod (or wire/rail) 1640 being attached or joined at the long end 1625. In one embodiment, the transition section 1620 can be absent, in which case the guide catheter extension includes the push rod or tube 1640 directly attached to the tube portion 1610. Further, although it is shown that the transition section 1620 includes a straight taper 1623 from the side view, it is understood that various other shapes for the taper can also be used, e.g., a convex curve, a concave curve, a curvilinear curve, or other more complex shapes (sinusoidal) (see e.g., the transition sections shown in FIGS. 14A, 15A, 15B, 15C), such that a generally slanted lumen opening or mouth is formed which contains a generally decreased, enclosed circumferential portion along the longitudinal axis L of the catheter away from the distal end 1609 (at the short end 1621, the enclosed circumferential portion is nearly 360 degrees, i.e., a full tube, while at the long end 1625 the enclosed circumferential portion can be much smaller, e.g., from 10 degrees to about 50 degrees). The skived transition section 1620 and the triplex cut-pattern tube portion 1610 can be made from a same or single tube by laser cutting creating a single frame or sections. Alternatively, the tube could be composed of several different frames or sections situated or laid end-to-end about a common center axis. The push rod (or wire/rail) 1640, which can be made from a metallic material, such as stainless steel, can be joined with the skived transition section 1620 by welding, interlocking or other any other bonding or fusing method.

Figure 14B:
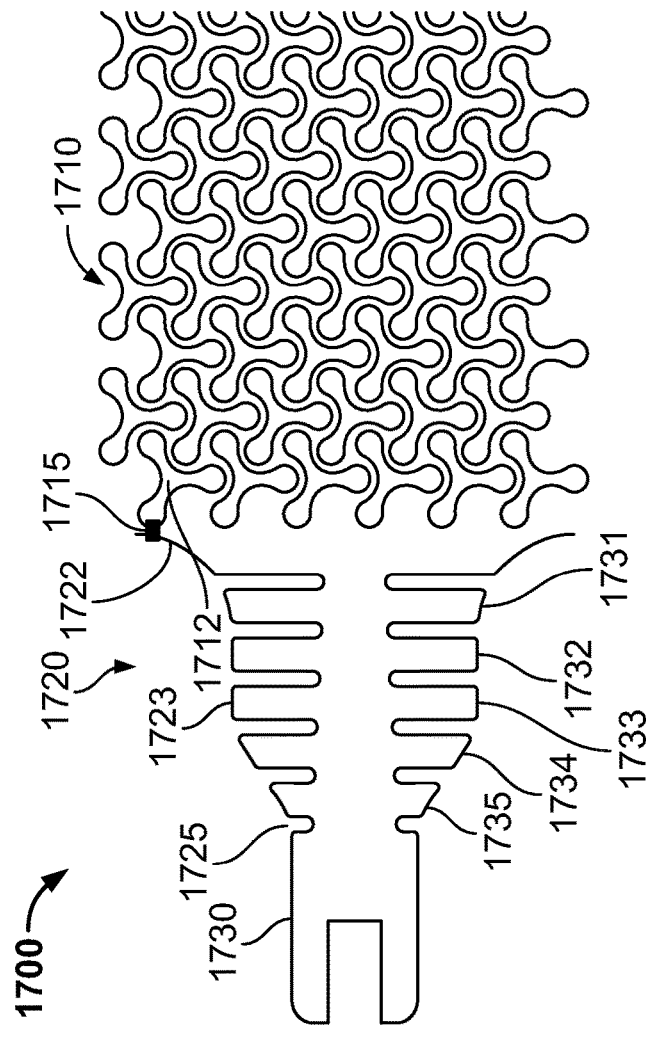
FIG. 14B is an unrolled or flat view of a portion of a guide catheter extension including a single triplex pattern zone according to one embodiment of the present invention.
Figure 14C:
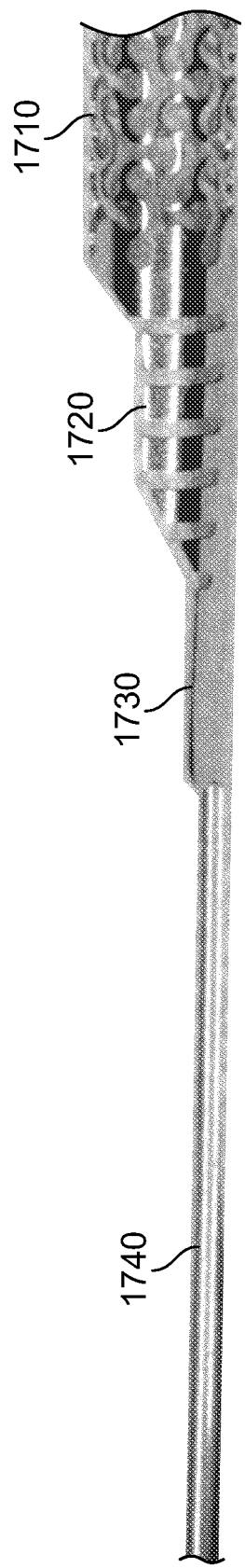
FIG. 14C is a photo of the portion of the guide catheter extension having the cut-pattern shown in FIG. 14B.

FIG. 14B shows a flat or unrolled view of a portion of a guide catheter extension 1700. FIG. 14C shows a photo of the portion of guide catheter extension shown in FIG. 14B. The portion of guide catheter extension 1700 includes a tube 1710 having a single triplex pattern (where all units have the same cutout segments, i.e., the same open surface area and cut-pattern perimeter length), a skived collar transition section 1720 which has a generally tapered edge having a short end 1722 and a long end 1725, and an attachment tab 1730 which is welded or bonded together with a push rod (wire/rail) 1740. As discussed above, all of 1710, 1720, and 1730 can be cut from a single tube by laser. At the short end 1722 of the transition section 1720, a cut 1715 can be made from an edge of the transition section 1720 through a closest triplex unit feature 1712. The width of the cut 1715 can vary. This cut allows the tube 1710 to expand or open up under pressure during manufacturing the catheter assembly when the tube is passed over a mandrel. The pattern of cuts shown in 1723 can vary. In the embodiment shown in 14B, the pattern forms a square wave pattern with a descending size, i.e., 1731, 1732, 1733, 1734, 1735. In the embodiment shown, when rolled into a tube, the two square wave patterns come together to form a cage like structure which is flexible, allowing for entire structure to be maneuvered through a tortuous path or anatomy.

Figure 14D:
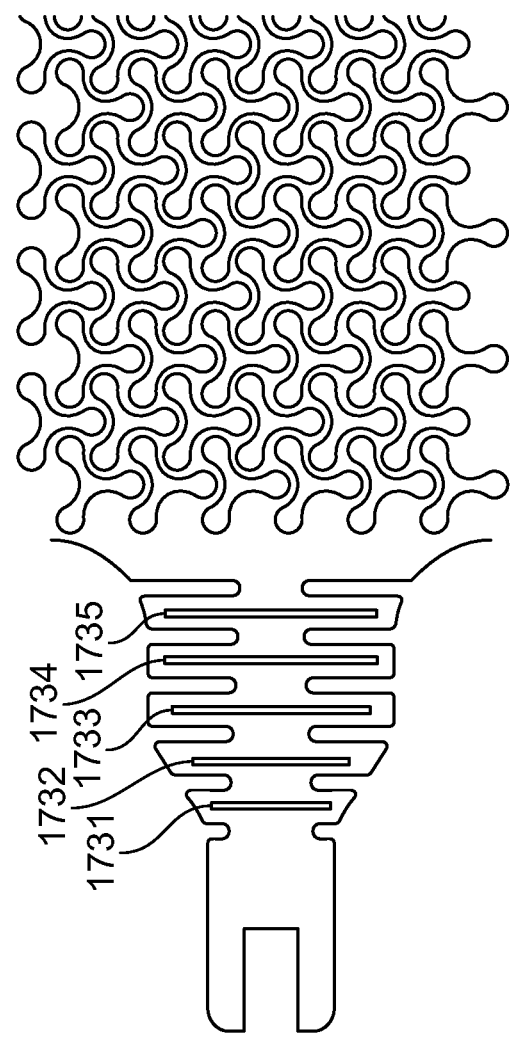
FIG. 14D shows a detail of a portion of FIG. 14B having transverse cuts.

In one embodiment, transverse cuts made be introduced in the portion of the pattern showing the square wave pattern in order to increase flexibility of the section, 1731, 1732, 1733, 1734, 1735. FIG. 14D. The width of the transverse cuts may also vary depending on the degree of flexibility required. Although schematically, the transverse cuts are shown as lines in the figure, other designs may be used, including a square wave, sinusoidal or meandering pattern.

As illustrated in FIGS. 15A-15B, the invention provides for a tube 1800 (or more particularly, a guide catheter extension) that includes a distal (full) tube portion 1810, a skived collar transition section 1820 having a generally tapered edge with varying degrees of an enclosed circumferential wall portion (forming a slanted lumen opening) which has a short end 1821 and a long end 1825, and a push rod (wire/rail) 1830 connected to the long end 1825 of the skived collar transition section 1820. The tube portion 1810 of the catheter can include a generally longitudinal cut-pattern 1880 such that the side wall of the tube portion 1810 (and the lumen enclosed therein) can be slightly opened upon an expansion force to facilitate manufacturing of the inner luminal portion of the tube or insertion of an interventional device into the slanted lumen opening of the transition section. Although schematically, the longitudinal cut is shown as a saw tooth line in the figure, other designs may be used, including a square wave, sinusoidal zig-zag, square-wave or meandering pattern; the width of the longitudinal cut can vary and periodicity, i.e., a repetitive pattern is not required. For example, the cut-pattern can be a straight line oriented in parallel with the long axis L of the catheter.

FIG. 15C shows the catheter 1800 where the tube portion 1810 has cut-pattern 1880. The cut-pattern 1880 can start from the short end 1821 and can extend either partially or fully along the tube. As illustrated in FIGS. 15A and 15B, the tube portion 1810 may join with another tube portion 1850 which does not contain a generally longitudinal cut pattern. The tube portion 1850, however, can contain other cut patterns, such as spiral cuts, interrupted spiral cuts, or triplex cut patterns as described herein.

Figure 15D:
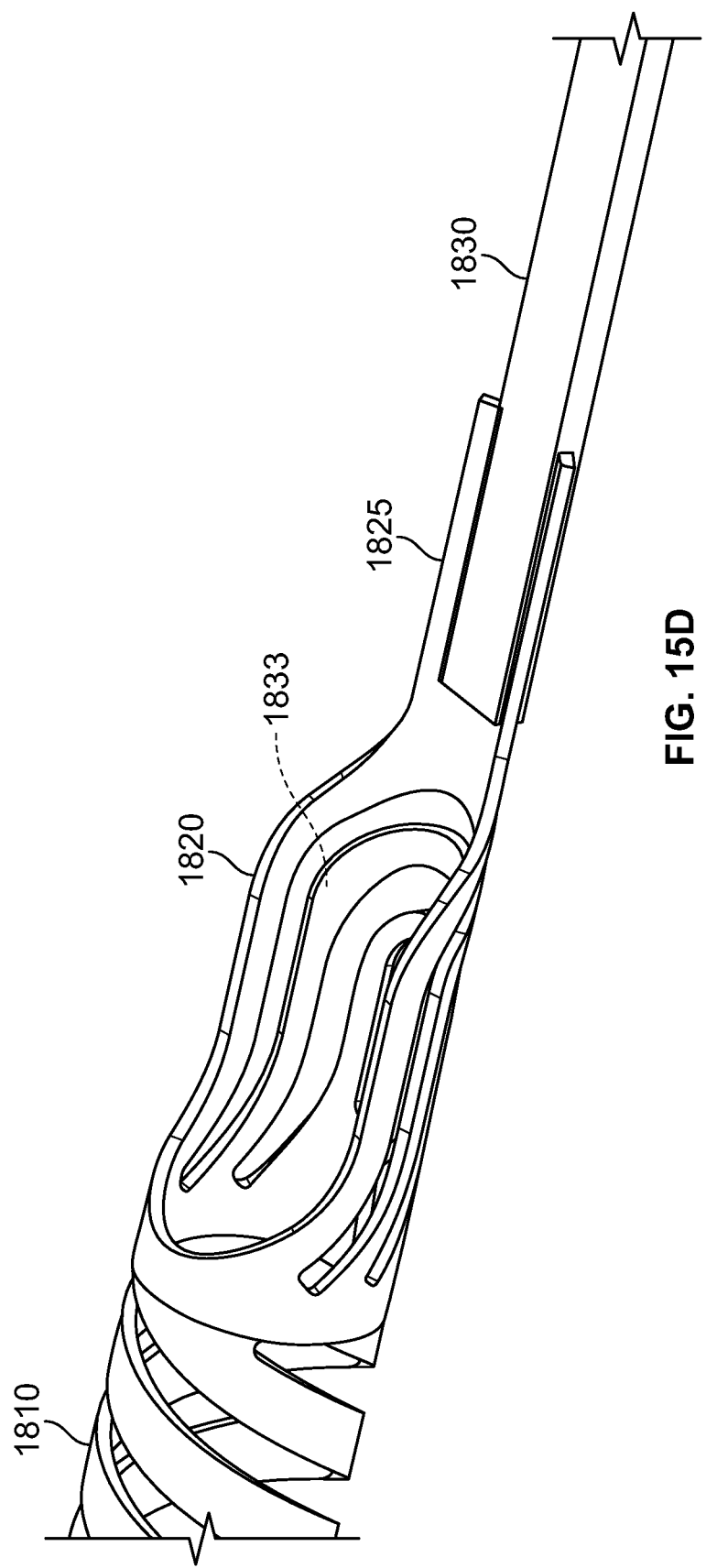
FIG. 15D is a 3D rendering of the guide catheter extension in 15A.
Figure 15E:
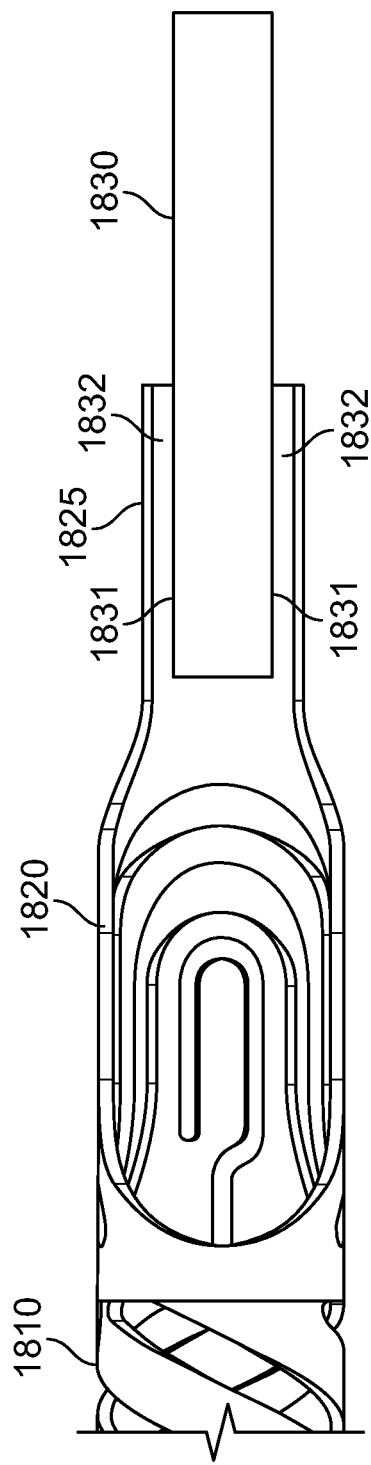
FIG. 15E is a 3D rendering of a top down view the guide catheter extension in 15D.
Figure 15F:
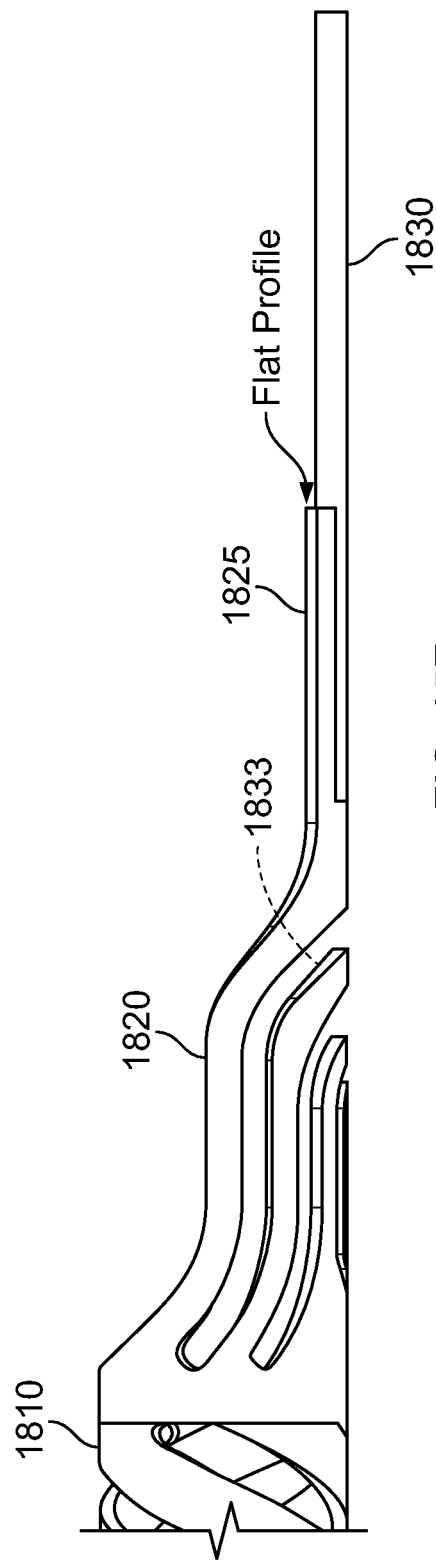
FIG. 15F is a 3D rendering of a side view the guide catheter extension in 15D.

FIGS. 15D-15F show a 3D rendering of the skived collar transition section 1820 and the push/rod 1830. The push rod 1830 may be formed from a separate piece and fused to long end 1825 at the junction formed between 1832 of the long end 1825 and 1831 of the push rod 1830 by any bonding method, including, crimping, swaging, staking. Adhesive bonding, welding, brazing or soldering may also be used. The design of the joint is shown as a rectangular opening in the long end 1825. Any shape can be used in a lock and key framework so that the push rod 1830 could snap fit into the long end 1825. As shown in FIG. 15F, the profile of the push rod 1830 is flat with respect to the lumen 1833 formed by the long end 1825.

Figure 16A:
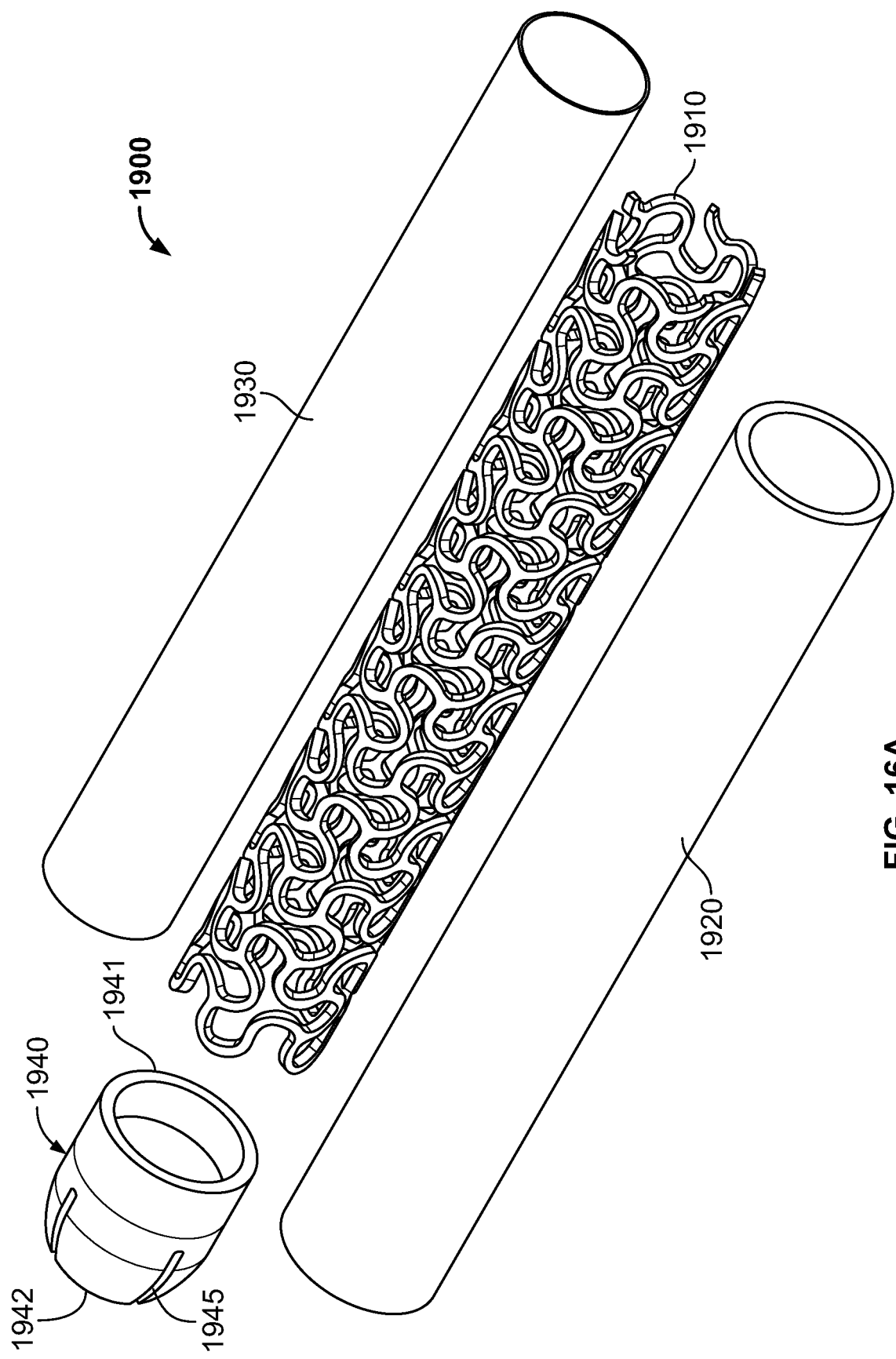
FIG. 16A shows certain components of a distal portion of a catheter according to an embodiment of the present invention.
Figure 16B:
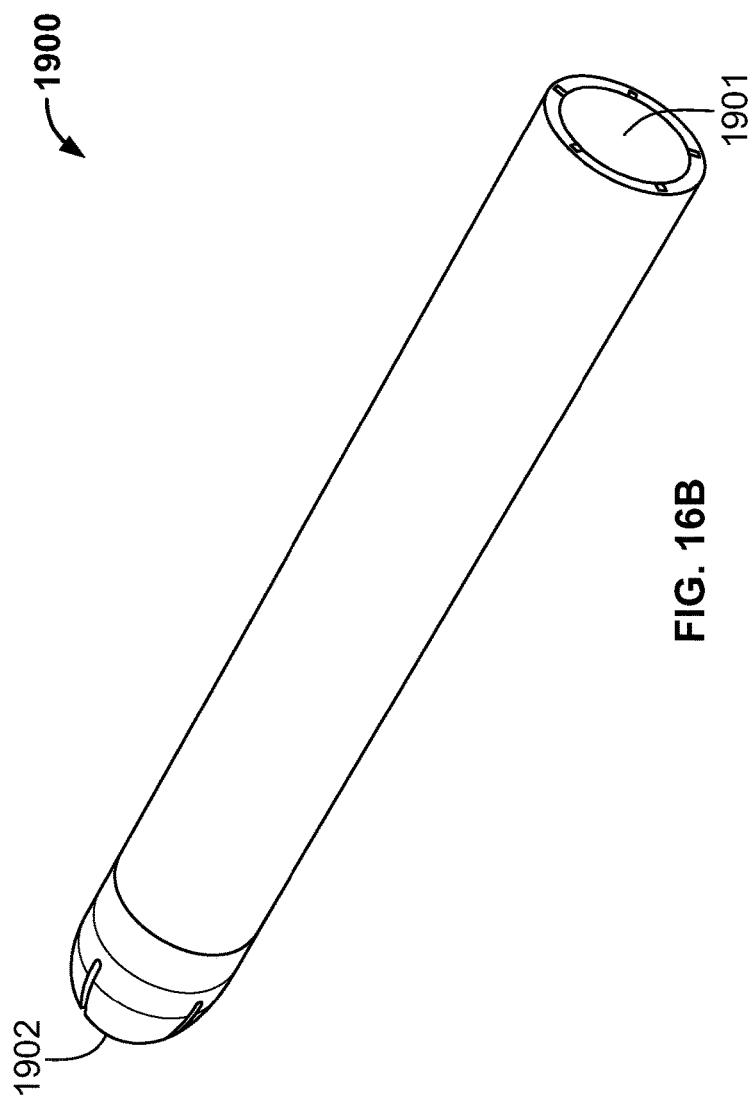
FIG. 16B shows the distal portion as assembled from the components shown in FIG. 16A.
Figure 16C:
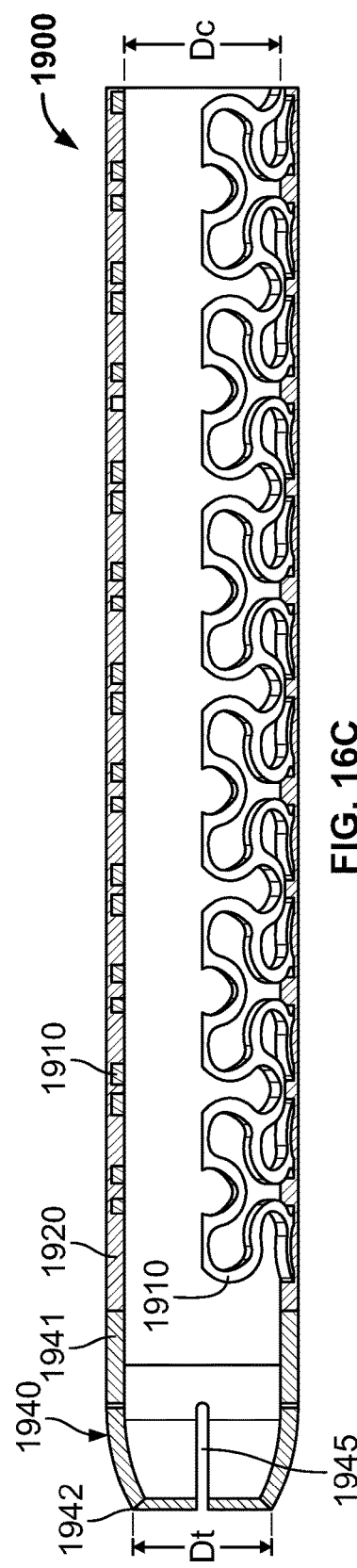
FIG. 16C shows a partial sectional view of the distal portion as depicted in FIG. 16B.
Figure 16D:
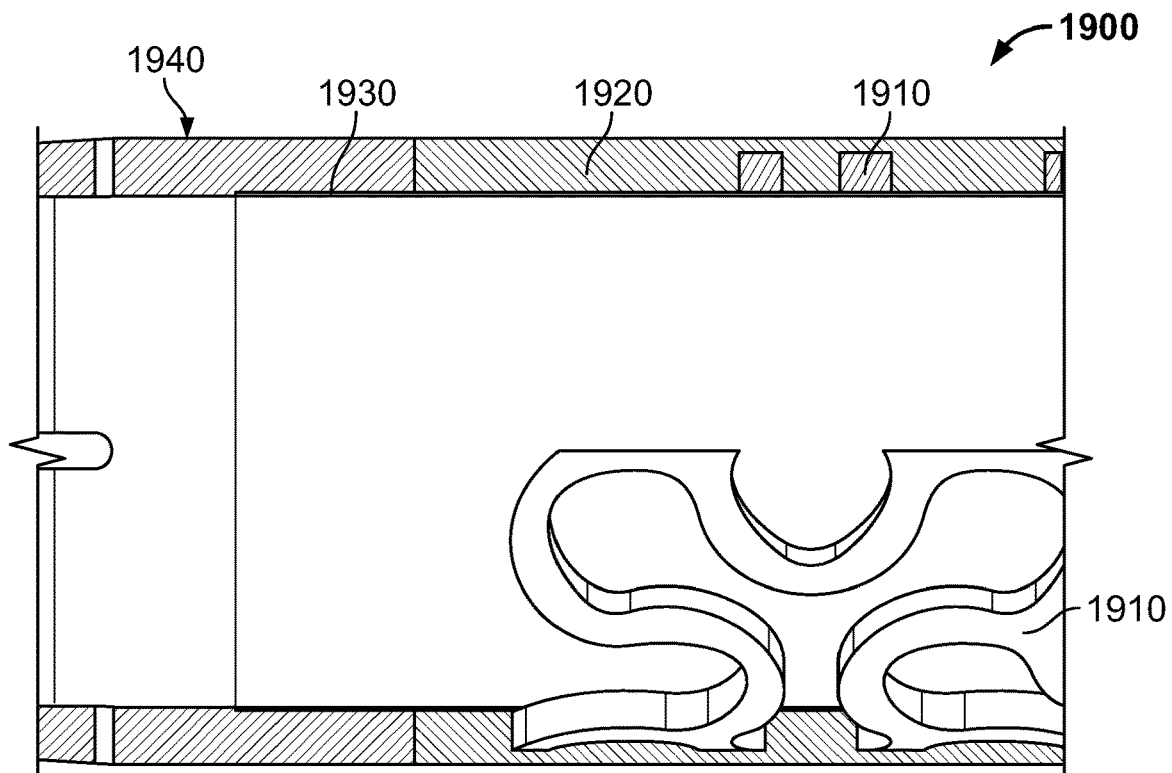
FIGS. 16D-16E show partial sectional views of various parts of the distal portion as depicted in FIG. 16B.
Figure 16E:
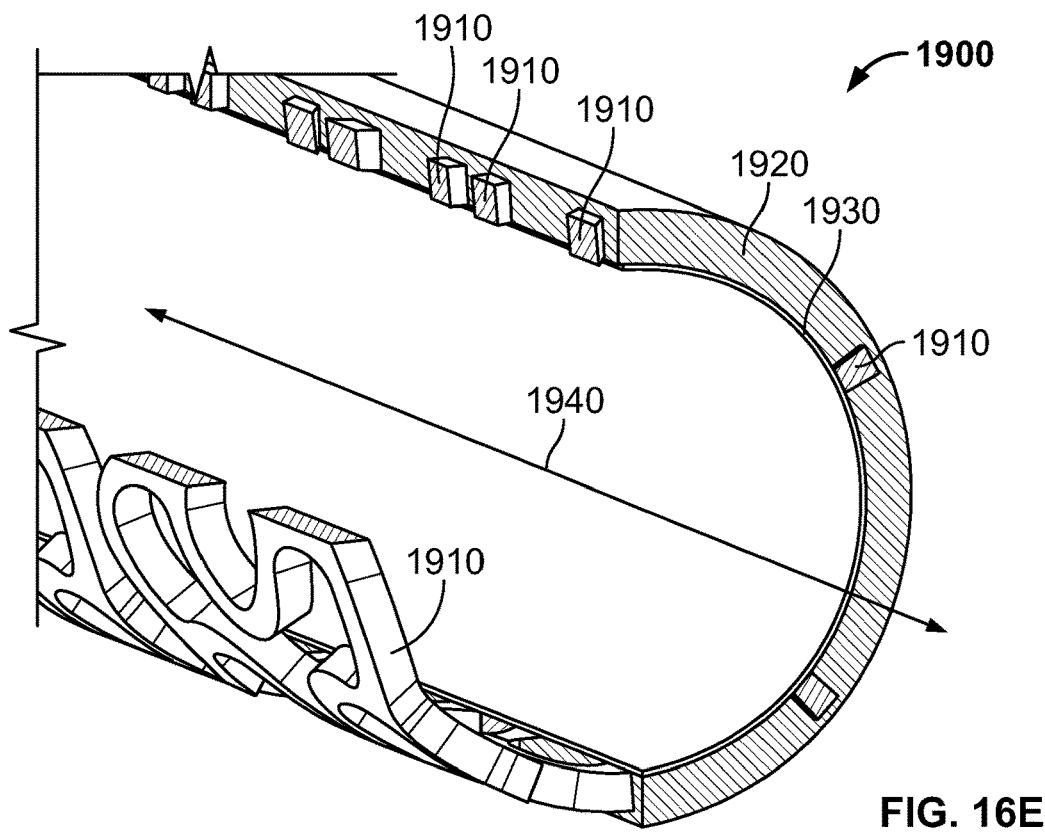

FIG. 16A shows certain components of a distal portion 1900 of a catheter tube (e.g., a guide catheter extension) according to an embodiment of the present invention. FIG. 16B shows the distal portion 1900 as assembled from the components shown in FIG. 16A. FIG. 16C shows a partial sectional view of the distal portion 1900 as assembled; FIGS. 16D and 16E show partial views of a portion of the distal portion 1900 as assembled near the distal tip (FIG. 16D) and a portion of the distal portion 1900 as assembled away from the distal tip. As shown in FIGS. 16A-16E, the distal portion 1900 having a proximal end 1901 and a distal end 1902, and includes a skeletal tubular frame 1910 having a single triplex cut pattern, an outer jacket 1920, an inner liner 1930, and a distal tip 1940 disposed at the distal end 1902. The term skeletal tubular frame refers to the tube described previously in FIGS. 2(A)-(D)-13, inclusive.

The tip portion has a proximal end 1941 and a distal end 1942, where the distal end 1942 form an inwardly bending curve forming an opening that has a diameter Dt smaller than that of the lumen Dc of the catheter tube. The distal tip 1940 near the distal end 1942 can include a number of cuts 1945 to make the distal tip more bendable, i.e., smaller "nose cone" like end in order to minimize trauma of the blood vessel wall when the distal tip is being advanced into a patient's vasculature. Alternatively, the distal tip may have a straight tube configuration. The tip portion 1940 can be made from a polymeric material into which a radiopaque material can be embedded or attached. Radiopaque fillers include gold, platinum, barium sulfate, bismuth subcarbonate, bismuth oxychloride, bismuth trioxide and tungsten (http://www.fostercomp.com/products/radiopaque-additives, retrieved Nov. 1, 2015).

The outer jacket 1920 can be made from a polymeric material, such as polyether block amide (e.g., PEBA®); the inner liner 1930 can also be made from polymeric material having improved lubricity, such as PTFE. The jacket can be made from a polymer, e.g., by enclosing the catheter tube with a co-extruded polymeric tubular structure of single of multiple layers and heat shrinking the tubular structure, or coating the catheter tube by dip coating or spraying. See, e.g., US20040142094. Alternatively, the outer jacket can be applied by electrospinning using various polymers, e.g., PTFE to create a fibrous mesh outer layer.

The polymer jacket material can be formed from nylon, polyether block amide, PTFE, FEP, PFA, PET, PEEK, etc. Further, the distal catheter portion (or the entire length of catheter) may be coated with a hydrophilic polymer coating to enhance increase lubricity when advancing through the parent guiding catheter or vascular anatomy. Hydrophilic polymer coatings can include polyelectrolyte and/or a non-ionic hydrophilic polymer, where the polyelectrolyte polymer can include poly(acrylamide-co-acrylic acid) salts, a poly(methacrylamide-co-acrylic acid) salts, a poly(acrylamide-co-methacrylic acid) salts, etc., and the non-ionic hydrophilic polymer may be poly(lactams), for example polyvinylpyrollidone (PVP), polyurethanes, homo- and copolymers of acrylic and methacrylic acid, polyvinyl alcohol, polyvinylethers, maleic anhydride based copolymers, polyesters, hydroxypropylcellulose, heparin, dextran, polypeptides, etc. See e.g., U.S. Pat. Nos. 6,458,867 and 8,871,869.

Figure 16F:
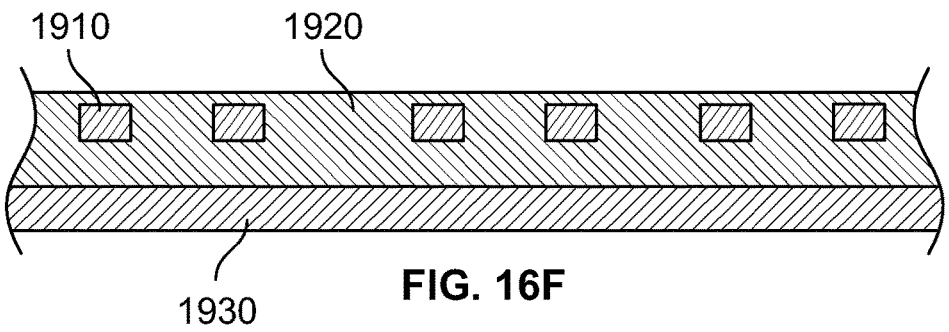
FIGS. 16F-16G show partial sectional views of various parts of the distal portion of a catheter according to an embodiment of the present invention.
Figure 16G:
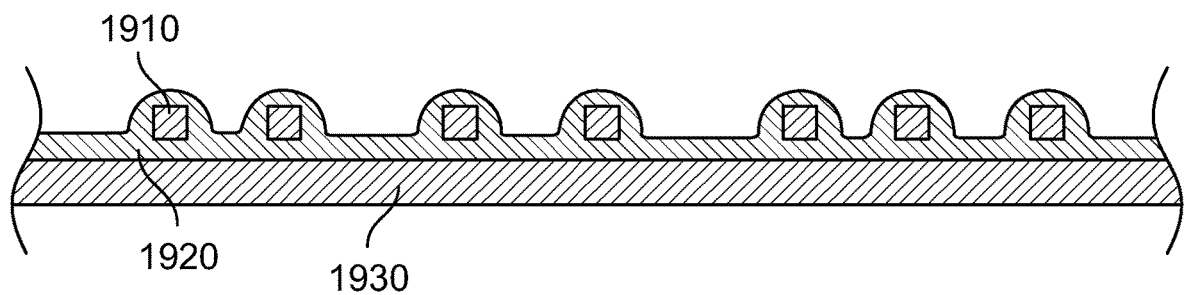

The components shown in FIGS. 16A-16E can be assembled by heat shrinking the outer jacket 1920 onto the skeletal tube frame 1910, which can fully embed the uncut or remaining portions of the patterned tube wall, i.e., the skeletal frame. FIGS. 16E and 16F. The inner liner 1930 can then be adhered with the outer jacket 1920 by heat or other bonding methods (note, the outer jacket is shown with stippling and the inner lining is shown with cross hatching). The inner liner may be incorporated in the covering process for the outer jacket, but the degree to which it is incorporated is material dependent. As shown in FIG. 16D, the inner liner 1930 can extend distally beyond the distal end of the skeletal tube 1910 and directly fused with the body of the distal tip 1940. In FIGS. 16A-16G, the outer jacket and inner liner are used to encapsulate the skeletal frame 1910. The skeletal frame 1910 is also bound to the outer most surface of the inner liner 1930, as shown in FIG. 16G. Additionally, dip coating and forming a conformal cover as the outer surface, allows for capturing or embedding the skeletal frame (tube) between the layers thereby creating a composite outer jacket material. The tube itself or the skeletal tube frame can have a triplex, spiral or a combination of patterns or contain linked tubular portions as described here. Once fully assembled with the outer jacket 1920 and inner layer 1930, the interior portion of the tube 1940, i.e., the lumen of the tube, is then completely enclosed within the skeletal tube frame 1920, the inner liner 1930 and the outer jacket 1920. The skeletal frame, i.e., the tube, can also be used directly without an outer jacket or inner lining. When using either a coated or uncoated skeletal tube frame, the driving design factor is maintaining the flexibility of the tube as discussed previously.

Figure 17A:
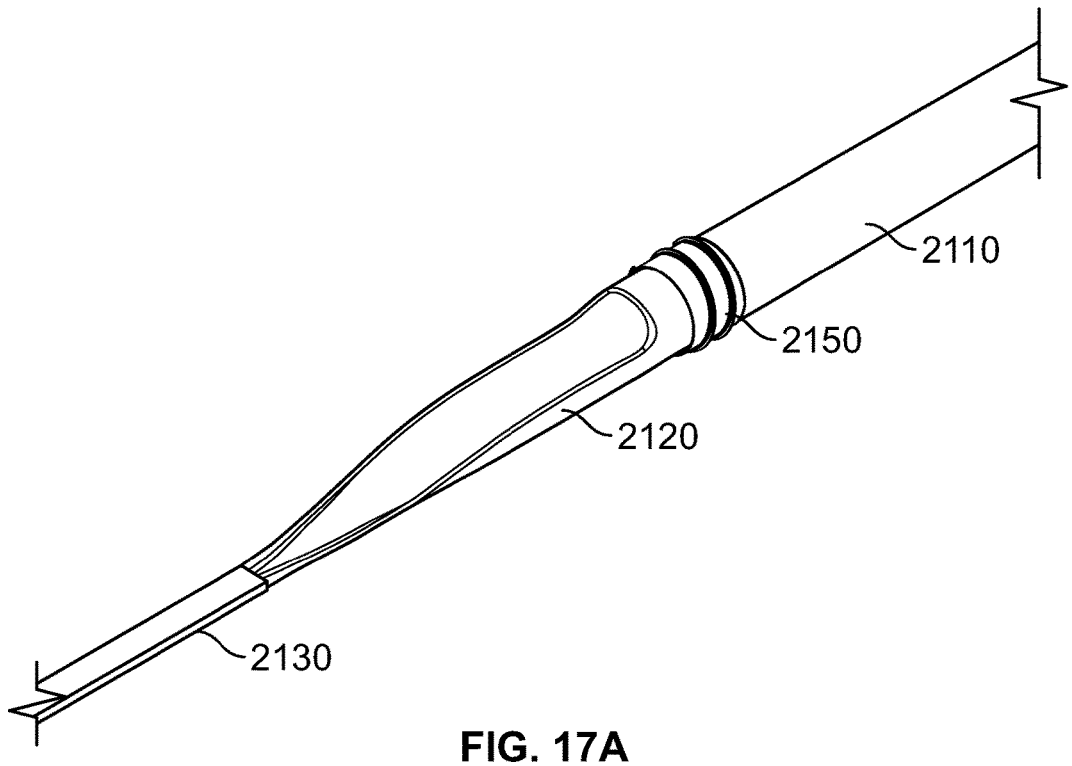
FIG. 17A shows a guide catheter extension having an attached sealer according to one embodiment of the present invention.

The guide catheter extension can include a tube portion 2110 having a fully enclosed lumen, a skived collar transition section 2120 adjacent the distal tube portion 2110 and having a generally tapered edge, and a proximal push rod (wire/rail) 2130 attached to the transition section 2120. As illustrated in FIG. 17A, a sealer 2150 can be fitted on the distal tube section 2110 and near the transition section 2120 to reduce the gap between the guide catheter extension and the surrounding guide catheter.

The sealer 2150 can take various forms or configurations, as illustrated in FIGS. 17B-17D. As shown in FIGS. 17B and 17C, the sealers 2156 and 2157 can be formed with a tubular base 2155 and 2162, respectively, for engaging with the distal tube portion 2110. The sealer 2155 can include a lateral extension or fin 2154 spirally wound about the tubular base 2152. Alternatively, the sealer 2157 can include wiping blade surfaces composed of a single or multiple set of fins or ridges 2164 that are wound circumferentially about the tubular base 2162 (i.e., perpendicular to the long axis of sealer). Alternatively, the sealer 2158 can take the form of a spiral extrusion or filament 2172.

The sealer, 2156, 2157, 2158, can be made with various elastic polymeric material, preferably rubbery material having good lubricity, such as PEBA, PTFE, silicon, polyurethane or other fluoropolymers. It can be fitted on the distal tube portion of the inner catheter by physical attachment (e.g., elastic or frictional engagement), chemical bonding, adhering, welding, gluing, heat fused or any other bonding method. The inner diameters 2155, 2165, and 2175 of the respective sealers 2156, 2157, and 2158 can be substantially the same as, or slightly smaller than, the outer diameter of the distal tube portion of the guide catheter extension. The fins and the base in sealers 2154, 2164 and 2152, 2162, respectively, can be made from the same material, or different materials. The heights of the fins of sealers 2154, 2164, and the diameter of the spiral wire 2172 can be selected according to the inner diameter of the guide catheter. The outer diameter of the sealer(s) (including the height of the fin(s) in 2154/2164, and the diameter of the spiral wire 2172) can be substantially the same as the inner diameter of the lumen of the guide catheter. The thickness of the fins can be selected such that the fins have sufficient pliability to allow the guide catheter extension to move axially within the guide catheter without significantly hampering its maneuverability or tactile feedback to the physician, while remaining sufficient obstructive to impede flow or back flow of bodily fluids caused by the suction or aspiration on the outer surface of the catheter body.

Figure 18A:
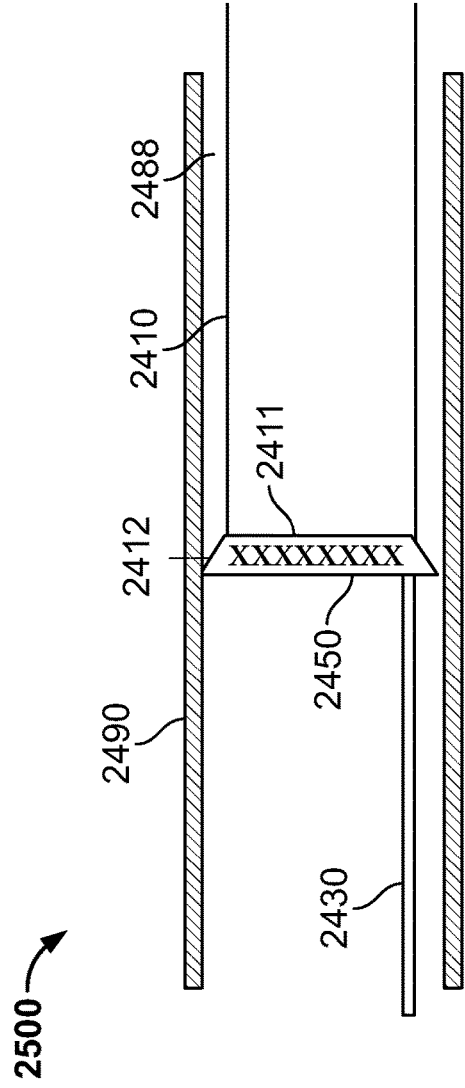
FIG. 18A is a schematic side view of a guide catheter extension having an end with a flared bib contained in a guide catheter, according to some embodiments of the present invention.
Figure 18B:
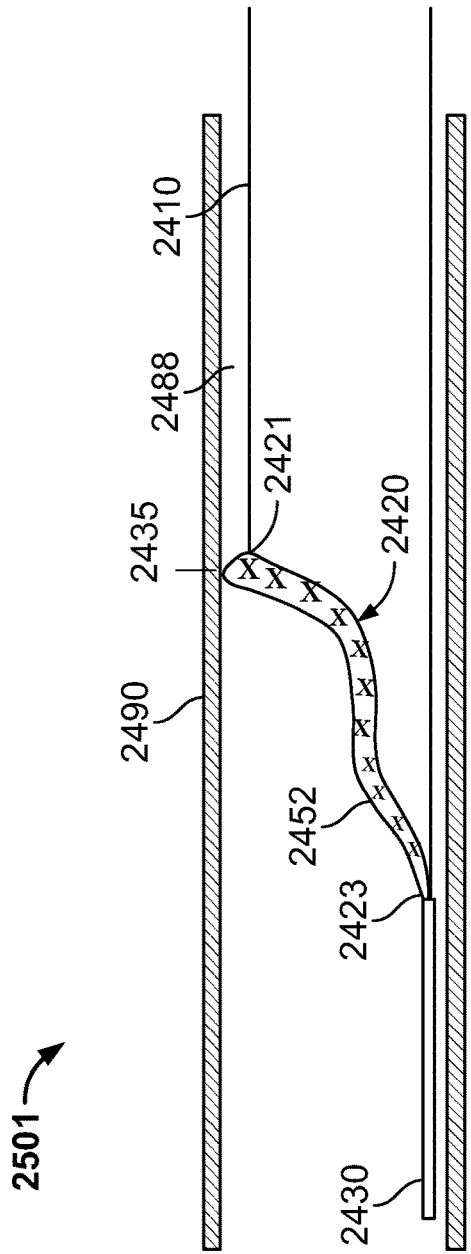
FIG. 18B is a cross-sectional view of the guide catheter extension and the guide catheter depicted in FIG. 18A.

The guide catheter extension can have a flare or flange 2452. The flare or flange can be used to close or reduce the gap between the guide catheter extension and an enclosing guide catheter. As illustrated in FIGS. 18A and 18B, a guide catheter extension 2500 can include a tube 2410 having a proximal end 2411, which is connected to a push rod 2430. At the proximal end 2411 there is a radially outwardly extending flare 2450, that may be substantially perpendicular to the long axis of the tube, which has a greater diameter than the outer diameter of the tube portion 2410, allowing a seal by a bib 2412 to form between the guide catheter extension and the guide catheter 2490. In this embodiment, the tube terminates and then transitions directly to the push rod 2430 without a transition through a skive.

Alternatively, the guide catheter 2501 can include a distal tube portion 2410, a skived collar transition section 2420 adjacent the distal tube portion 2410 and a generally tapered edge having a short end 2421 and a long end 2423, and a push rod 2430 connected to the long end 2423 of the transition section. A flare or flange 2452 extends radially outwardly from the lumen opening formed by the tapered edge, and has a greater diameter than the outer diameter of the tube portion 2410. Thus, like the sealers described in connection with FIGS. 17A-17D, and the flare or flange described in connection with FIG. 18A, the flare or flange can substantially close or seal the gap 2488 by a bib 2435 formed between the guide catheter 2490 and the tube 2410, which may be covered by an outer jacket. This type of construction enables the guide catheter 2490 and the guide catheter extension 2500, 2501 to be used to inject contrast media into a target site in the patient's vasculature without leakage from the distal end of the guide catheter, i.e., the end closest to the push rod 2430. The flare together with the bib can also be used to facilitate smooth insertion of an interventional device, such as a balloon catheter or a stent.

Like the sealer described previously, the flares described in connection with FIGS. 17A-17B can be made from an elastic polymeric material, preferably rubbery material with good lubricity, such as PEBA, PTFE, silicon or other fluoropolymers. The thickness of the flare can be selected to ensure the flares have sufficient pliability to allow the guide catheter extension to move axially within the guide catheter without significantly hampering its maneuverability. For example, the thickness of the flare can be about 0.1 mm to about 1 mm, or about 0.2 mm to about 0.5 mm. The flares can be made as a separate piece and adhered to the proximal end 2411 (in FIG. 18A) or the lumen opening of the transition section 2420 (in FIG. 18B), or made as an extension of an inner lining or outer jacket of the catheter extension 2400a or 2400b.

Figure 19:
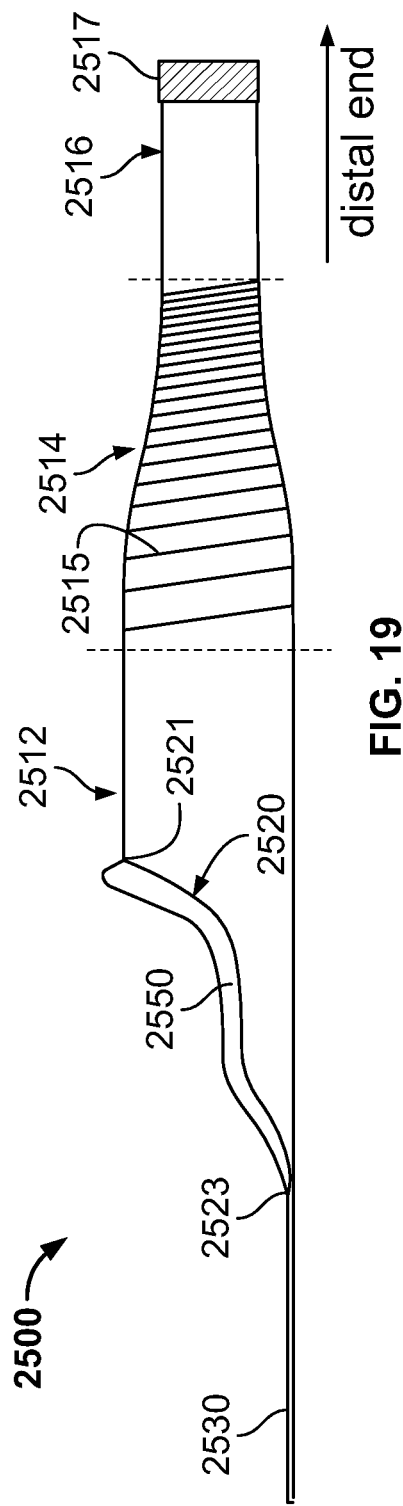
FIG. 19 depicts a guide catheter extension having a skived collar transition section with a flared bib and a tube portion having varying diameter.

In one embodiment, and as illustrated by FIG. 19, the invention provides for a guide catheter extension 2500 that includes a first tube portion 2512, a second tube portion 2514 that has a gradually decreased diameter distally, and a third tube portion 2516 which is at the distal end of the guide catheter extension and that can include a radiopaque tip 2517. The narrowing in diameter of the first and second tube portion may be produced by shape training of the nitinol tube using standard heating technology (see http://www-personal.umich.edu/~btrcase/share/SMA-Shape-Training-Tutorial.pdf, retrieved Nov. 1, 2015). The skived collar transition section 2520 is disposed adjacent the first tube portion 2512. The transition section 2520 has a generally tapered edge having a short end 2521 and a long end 2523, and a flange 2550 extends radially outwardly from the slanted lumen opening formed by the tapered edge. A push rod 2530 is attached to the transition section 2520.

To use as an injection or aspiration system, both the guide catheter and the distal tube portion of the guide catheter extension should have a tube wall impermeable to fluid. Such impermeable tube wall can be made of a solid tube (made from a metal, a polymer, optionally with embedded braid or other reinforcing material), or made from a tube having spiral-cut or other cut patterns (such as the triplex cut patterns described herein) and sealed with a fluid-impermeable jacket, e.g., PEBA, nylon, PTFE, silicon or other material. The invention also provides for an aspiration system including a guide (or outer) catheter having a guide catheter lumen, an inner catheter (e.g., a guide catheter extension) movable within the inner guide catheter lumen, and the outer edge of a sealing member on the inner catheter. The inner catheter can be a guide catheter extension which can generally take the form of those described herein.

Each of the first tube portion 2512 and the second tube portion 2514 can be made from a metal or metal alloy (such as stainless steel (spring steel) or nitinol), or a braid or coil supported polymer material. The second tube portion 1514 can include a spiral cut-pattern 2515, and the pitch of the spiral cut can be gradually decreased distally. An outer jacket and an inner lining can be coated onto the spiral-cut section to seal off the openings of the spiral cuts. The third tube portion 2516 can be made from a material or construction more flexible or pliable than the material or construction for the first and the second tube portions 2512 and 2514. For example, the third tube portion 2516 can be formed from a polymeric material without a wire or braid support. In general, the flexibility of the three tube portions 2512, 2514, and 2516 decreases distally. The flare and the bib together with the distally decreased lumen diameter allows easy insertion of variable-sized (diameter) interventional devices, such as micro-catheters, balloon catheters, and stents, into the lumen of the guide catheter extension 2500.

Figure 20:
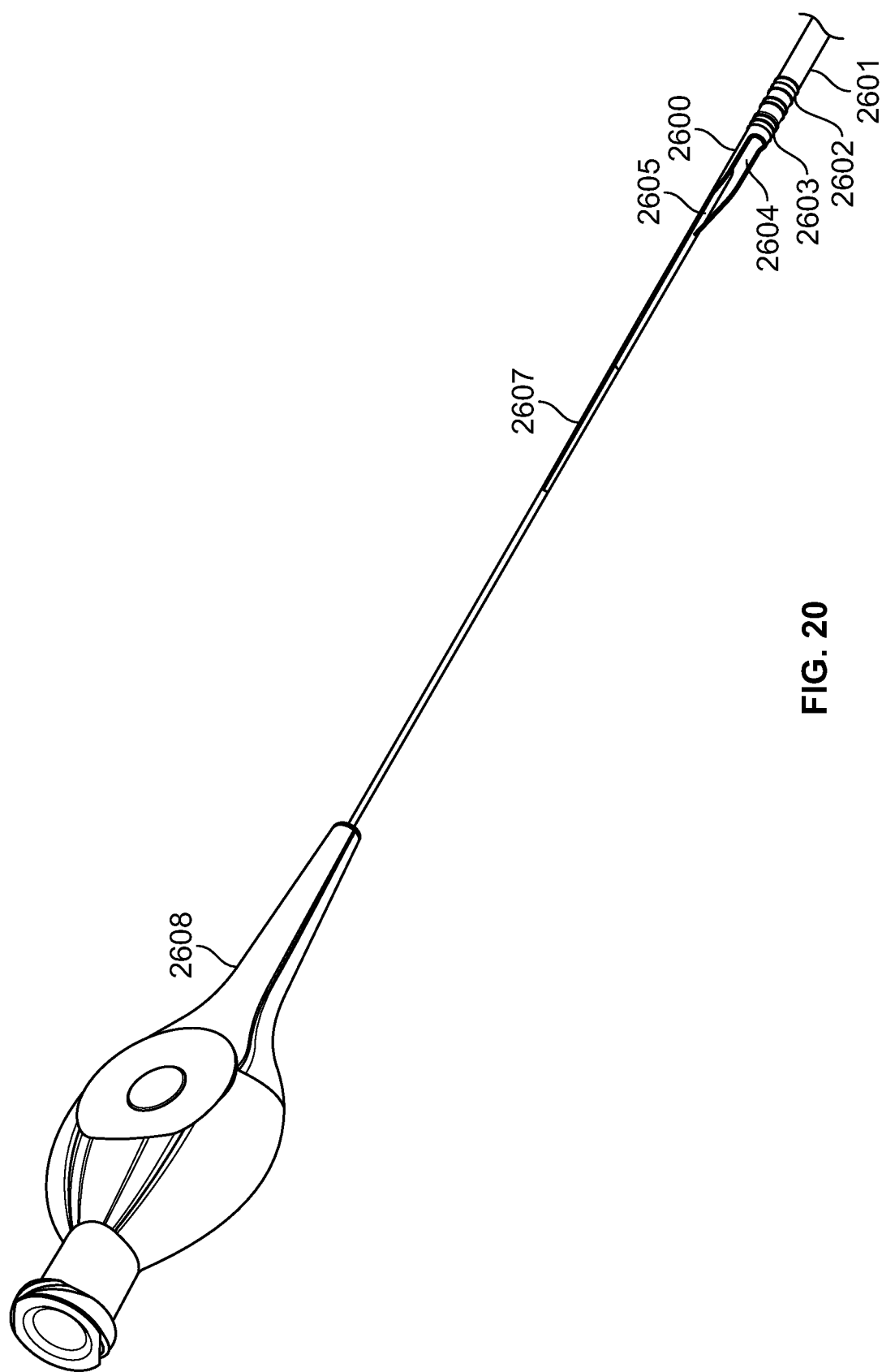
FIG. 20 shows the guide catheter assembly with an assembled handle.

The guide catheter extension can be assembled together with a handle for pushing or torqueing. FIG. 20 depicts one embodiment of the non-functional catheter hub, holding tap or maneuvering hub which can provide aid in torqueing the device once inside the anatomy, 2608. The push rod 2607 is fused to the long end 2600. The lumen 2604 runs through the guide catheter extension 2601. In the embodiment shown, there are two sealers configurations 2603 and 2062.

The scope of the present invention is not limited by what has been specifically shown and described hereinabove. Those skilled in the art will recognize that there are suitable alternatives to the depicted examples of configurations, constructions, and dimensions, and materials. The citation and discussion of any references in the application is provided merely to clarify the description of the present invention and is not an admission that any reference is prior art to the invention described herein. All references cited and discussed in this specification are incorporated herein by reference in their entirety. While certain embodiments of the present invention have been shown and described, it will be obvious to those skilled in the art that changes and modifications may be made without departing from the spirit and scope of the invention. The matter set forth in the foregoing description and accompanying drawings is offered by way of illustration only and not as a limitation.

What is claimed is:

1. A guide catheter extension, comprising:
    a tube having a proximal end, a distal end, a longitudinal axis, and a transition section positioned at the proximal end of the tube, wherein the transition section defines an opening oriented substantially perpendicular to the longitudinal axis of the tube, wherein the tube further comprises a plurality of sections having different cut patterns therein, wherein each section has a different flexibility than the other sections, and wherein the tube has an increasing flexibility from the proximal end to the distal end;
    a push rod, wherein the push rod has a proximal and distal end, and is attached at a junction to the proximal end of the tube;
    a radiopaque tip positioned at the distal end of the tube, wherein the tip has a proximal and distal end, wherein the distal end of the tip has an inwardly bending curve on an interior surface thereof,
    an outer jacket, formed from a polymer, at least partially disposed on an outer diameter of the tube;
    an inner liner at least partially disposed within a lumen, wherein the inner liner is adhered to the outer jacket; and
    a radially outwardly extending flare that is adhered to the tube and that is configured to prevent the backflow of fluids.

2. The guide catheter extension of claim 1, wherein an outer diameter of the tube tapers from the proximal end to the distal end of the tube.

3. The guide extension catheter of claim 2, wherein the distal end of the push rod has a flat profile.

4. The guide catheter extension of claim 3, wherein the push rod is bonded at the junction.

5. The guide catheter extension of claim 1, wherein the push rod is a tube.

6. The guide catheter extension of claim 1, wherein the cut patterns include cutout portions having a three-fold rotational symmetry about a central point of symmetry.

* * * * *